(12) United States Patent
Van Wyk

(10) Patent No.: US 11,291,493 B2
(45) Date of Patent: Apr. 5, 2022

(54) SIMPLIFIED METHODS FOR NON-INVASIVE VASECTOMY

(71) Applicant: Robert A. Van Wyk, St. Pete Beach, FL (US)

(72) Inventor: Robert A. Van Wyk, St. Pete Beach, FL (US)

( * ) Notice: Subject to any disclaimer, the term of this patent is extended or adjusted under 35 U.S.C. 154(b) by 0 days.

(21) Appl. No.: 17/338,115

(22) Filed: Jun. 3, 2021

(65) Prior Publication Data

US 2021/0290291 A1 Sep. 23, 2021

Related U.S. Application Data

(63) Continuation-in-part of application No. 17/150,313, filed on Jan. 15, 2021, now abandoned, which is a continuation-in-part of application No. 16/700,393, filed on Dec. 2, 2019.

(60) Provisional application No. 62/995,188, filed on Jan. 16, 2020, provisional application No. 62/917,325, filed on Dec. 3, 2018.

(51) Int. Cl.
  *A61B 18/08* (2006.01)
  *A61B 18/12* (2006.01)
  *A61B 18/00* (2006.01)

(52) U.S. Cl.
  CPC ........ *A61B 18/085* (2013.01); *A61B 18/1206* (2013.01); *A61B 2018/00547* (2013.01); *A61B 2018/00589* (2013.01); *A61B 2018/126* (2013.01)

(58) Field of Classification Search
  CPC ........................................................ A61F 6/206
  See application file for complete search history.

(56) References Cited

U.S. PATENT DOCUMENTS

| | | |
|---|---|---|
| 3,762,417 A | 10/1973 | Textor |
| 4,803,983 A | 2/1989 | Siegel |
| 4,920,982 A | 5/1990 | Goldstein |
| 5,026,379 A | 6/1991 | Yoon |
| 5,203,785 A | 4/1993 | Slater |
| 5,445,638 A | 8/1995 | Rydell et al. |
| 5,667,518 A | 9/1997 | Pannell |
| 5,702,390 A | 12/1997 | Austin et al. |

(Continued)

*Primary Examiner* — Ronald Hupczey, Jr.
(74) *Attorney, Agent, or Firm* — Smith Patent, LLC; Chalin A. Smith

(57) ABSTRACT

Conventional vasectomy techniques suffer from a number of potential complications, including, for example, a substantial risk for the development of hematomas, and swelling, and post-surgical pain, a potential for spontaneous duct reconnection and undesired resumption of fertility, a need for a highly skilled surgical professional, as well as a long recovery period, accompanied by severe limitations on post-surgical activity. The vasectomy methods of the present invention reduce and/or minimize contact with sensory nerves located on the distal side of the vas deferens, particularly the distal region of the outer vas deferens sheath, so as to minimize nerve damage and the post-surgical pain associated therewith. In addition, the methods of the present invention overcome the disadvantages and deficiencies of the prior art, resulting in a rapid, reliable, minimally-invasive male sterilization procedure that may be readily, reliably and successfully performed by minimally skilled personnel around the world in a variety of medical settings.

12 Claims, 36 Drawing Sheets

(56) References Cited

U.S. PATENT DOCUMENTS

| | | |
|---|---|---|
| 5,797,958 A | 8/1998 | Yoon |
| 5,827,279 A | 10/1998 | Hughett et al. |
| 5,865,835 A | 2/1999 | Lolagne |
| 5,891,141 A | 4/1999 | Rydell |
| 5,972,002 A | 10/1999 | Bark |
| 6,610,060 B2 | 8/2003 | Mulier et al. |
| 6,843,789 B2 | 1/2005 | Goble |
| 8,220,464 B2 | 7/2012 | Pannell et al. |
| 8,561,615 B2 | 10/2013 | Pannell et al. |
| D886,297 S | 6/2020 | Van Wyk |
| D903,867 S | 12/2020 | Van Wyk |
| 2001/0031961 A1 | 10/2001 | Hooven et al. |
| 2002/0107517 A1 | 8/2002 | Witt et al. |
| 2003/0069571 A1 | 4/2003 | Treat et al. |
| 2003/0078577 A1 | 4/2003 | Truckai et al. |
| 2004/0158286 A1 | 8/2004 | Roux et al. |
| 2004/0249368 A1 | 12/2004 | Hooven |
| 2005/0033353 A1 | 2/2005 | Jones |
| 2005/0101952 A1 | 5/2005 | Lands et al. |
| 2006/0069388 A1 | 3/2006 | Truckai et al. |
| 2008/0077156 A1 | 3/2008 | Emstad |
| 2008/0105265 A1* | 5/2008 | Pannell ................ A61B 17/122 128/843 |
| 2010/0145381 A1 | 6/2010 | Moon |
| 2010/0288285 A1* | 11/2010 | Marmar ............... A61B 17/282 128/843 |
| 2020/0170831 A1 | 1/2020 | Van Wyk |

* cited by examiner

SIMPLIFIED METHODS FOR NON-INVASIVE VASECTOMY

PRIORITY CLAIMS

The instant application is a continuation-in-part of U.S. patent application Ser. No. 17/150,313 filed Jan. 15, 2021, which, in turn, both claims the benefit of U.S. Provisional Application Ser. No. 62/995,188 filed Jan. 16, 2020 and is a continuation-in-part of U.S. patent application Ser. No. 16/700,393 filed Dec. 2, 2019, which, in turn, claims the benefit of U.S. Provisional Application Ser. No. 62/917,325 filed Dec. 3, 2018. The contents of these prior applications are hereby incorporated by reference in their entirety.

TECHNICAL FIELD OF THE PRESENT INVENTION

The present invention relates to a method for performing a vasectomy without mechanically bruising the sensory nerves in the spermatic cord so as to thereby reduce post-procedural pain.

BACKGROUND OF THE PRESENT INVENTION

Vasectomy is a surgical procedure that typically involves the removal of a portion of the ducts that carry sperm out of the testes (i.e., the vas deferens), thereby stopping the flow of sperm from the testicle to the prostate gland; once the vas deferens is interrupted, the sperm cannot be delivered and the man is rendered sterile. Currently used vasectomy methods, such as the No Scalpel Vasectomy ("NSV"), require that each vas deferens be dissected from the scrotum to allow the clinician to occlude and divide the vas duct. Therein, the vas deferens is isolated, extracted, or otherwise delivered from the scrotum via one or two openings formed by puncturing the scrotum and then expanding the opening(s). The vas sheath is then retracted from a portion of the vas duct, which is then hemi-dissected and occluded, preferably by means of mucosal cautery in which the distal end of the filament of a battery powered cautery unit is inserted into each duct lumen and energized so as to create a luminal plug of scar tissue. Alternatively, vas occlusion may involve ligation with a suture or surgical clip. In either case, after the vas is divided, a portion of the duct is optionally excised and one end is isolated in the vas sheath to create a barrier to reconnection of the duct. For example, a layer of the vas sheath may be placed between the two severed ends of the vas duct in order to cover one end but not the other in a technique referred to as "fascial interpositioning". Once both ends are sufficiently secured, the duct is then returned to the scrotum, the opening through which the vas was accessed is allowed to close and the procedure is deemed complete.

While the procedure appears simple, significant surgical skill is required and complications may result. Most common of these is the arisal of hematomas caused by slow bleeders at the site of the duct occlusion and division. In non-elastic tissue, a small amount of bleeding is quickly stopped by the tension that develops in the tissue. However, because the scrotum is essentially an elastic balloon-like vessel, the hydrostatic pressure necessary to stop bleeding is not present. Accordingly, even the slightest amount of persistent bleeding can cause a tremendously large hematoma. In a similar manner, rough handling of the tissue can lead to significant swelling. Even the most experienced vasectomy surgeon will occasionally encounter these problems.

Other disadvantages inherent in conventional surgical vasectomy, as exemplified by the NSV, include the prolonged surgical duration, which is generally on the order of twenty minutes or more. In addition, conventional vasectomy procedures fail to adequately account for the natural tendency of the cut ends of the vas deferens to grow back together, thereby allowing the flow of sperm to the prostate and resumption of fertility. Means for avoiding this failure have been the subject of debate among those skilled in the art, the question being whether the vas deferens should be clipped, cut, cauterized, ligated, or all of the above. Finally, because sharp instruments are used, performing a vasectomy on HIV+ patients presents a risk to the surgeon.

In addition, vasectomy patients experience varying levels of post procedure discomfort. This may range from mild discomfort that disappears within a few days, to persistent pain that may require up to several weeks or more to dissipate. The spermatic cord formed by the vas deferens includes an inner vas duct and an outer sheath that surrounds the duct with sensory nerves located primarily in the portion of the sheath distal to the duct when a vasectomy is performed. In a typical NSV, after the vas sheath and the duct contained therein are isolated and exposed at an opening created in the patient's scrotum, an opening is formed in the vas sheath proximal to the surgeon to expose the duct. The duct is then grasped by an instrument and the sheath is retracted away from the clamp to expose a portion of the duct sufficient for occluding and dividing the duct. Retracting (stripping) the sheath from the duct to create this operative space has a tendency to bruise or otherwise damage sensory nerves in the portion of the sheath that is stripped back. Additional injury to the nerves may occur when one end of the duct is returned to the sheath, and the other end is secured outside the sheath so as to provide fascial interpositioning. It is believed that bruising and other trauma to these nerves is a contributing factor to post vasectomy pain.

In the above-referenced co-pending U.S. patent application Ser. No. 16/700,393 to Van Wyk that published as U.S. 2020/0170831 on Jun. 4, 2020 (hereinafter "Van Wyk '831") and to which the instant application claims priority, the present inventor discloses a method for sealing and dividing a vas duct. The method may be performed with the vas isolated outside the scrotum in the manner of a standard NSV, or, alternatively, in situ, without isolating the vas outside of the scrotum. In the earlier described methods, both the vas duct and the vas sheath are severed after sealing. However, for many clinicians, this is less desirable than retaining an intact vas sheath. Accordingly, there is a need in the art for a vasectomy method that provides reliable occlusion of the vas duct without causing post vasectomy pain due to injury of sensory nerves in the vas sheath.

SUMMARY OF THE PRESENT INVENTION

Disclosed herein are methods for performing a vasectomy in which the multiple steps required to occlude and divide a vas duct in a typical NSV are replaced by a simple sealing process followed by an optional dividing step. According to methods of the present invention, the duct is sealed in two locations spaced a predetermined distance apart without removing the duct from the sheath. Importantly, the sheath is not stripped back to expose a portion of the duct prior to sealing as this stripping process is known to cause injury to the sensory nerves present in the "back side" of sheath, i.e., the region of the sheath behind or distal to the vas duct. This eliminates the associated opportunities for injury to or bruising of nerves located in the vas sheath.

In the methods of the present invention, the vas sheath with its contained duct is isolated and optionally delivered from the scrotum through an opening or openings formed in the scrotum. In certain embodiments, the sheath and duct may be dissected from the scrotum through bilateral openings. In other embodiments, both ducts may be delivered through a single opening formed on the midline of the scrotum. In further embodiments, the duct is addressed in situ, without removal from the scrotum.

In either case, after the sheath and duct are located, a non-conductive or insulated clamp is applied to the duct within the sheath, at the midline of the duct, thereby minimizing contact with delicate sensory nerves present in the "back" or distal region of the sheath. The jaws of a radio frequency ("RF") bipolar coagulating instrument are positioned around the clamp and closed onto the tissue so as to apply a compressing force. Radio frequency energy from an electrosurgical generator is applied so as to heat the tissue between the bipolar jaws so as to coagulate and seal the tissue. The result is an arcuate region of sealed sheath tissue. Portions of the duct contained within this arcuate region are sealed within the sealed sheath tissue. Tissue circumscribed within the arcuate region (that is, surrounding the non-conductive clamp) is not coagulated. Optionally, while the jaws of the bipolar coagulating device remain in place, this tissue can be removed so as to divide the duct. This may be accomplished using the insulated clamp or another instrument. This removal is not essential since the uncoagulated region is circumscribed by the sealed region and accordingly has no blood flow to it. The tissue will naturally necrose and be absorbed by the body over time.

Because the non-conductive clamp is positioned at about the midline of the duct and the bipolar jaws of the sealing device that surround the clamp are narrow, the number of nerves that are clamped between the jaws is minimized. During sealing of the arcuate region, nerves between the jaws are destroyed by the heat and clamping force. Those that are in sufficiently close proximity to the jaws are destroyed by the RF energy and resulting heat, a process known as radio frequency neurotomy. The RF neurotomy technique is commonly used in other regions of the body to deaden pain producing nerves. In the context of the vasectomy methods of the present invention, it is a desirable byproduct of the sealing method.

In parent publication Van Wyk '831, the present inventor teaches a vasectomy method that may be performed outside of the scrotum, more particularly a method that includes bipolar occlusion of a portion of the vas deferens and subsequent removal of that vas portion that includes both the inner vas duct and the duct's surrounding sheath. In the context of this vasectomy method as previously described, the sealed ends of the separated duct and surrounding sheath are returned to the scrotum and the ends have independent mobility within the scrotum. In contrast, in the methods of the present invention, only a portion of the sheath is sealed and removed along with the vas duct segment. Critically, in the context of the present invention, contact with the distal region (or "back side") of the vas sheath that contains the bulk of the sensory nerves is avoided. In this manner, the sealed ends of the vas duct, as well as the sealed region of the sheath, remain connected, a preferred result that is akin to that achieved via the "non-divisional" Marie Stopes vasectomy methods described in greater detail hereinbelow. Namely, in the methods of the present invention, like those of Marie Stopes, a physical separation is maintained between the sealed duct ends while the principal nerve-containing region of the outer sheath is preserved.

These and other objectives can be accomplished by the invention herein disclosed. Further objects and features of the invention will become more fully apparent when the following detailed description is read in conjunction with the accompanying figures and examples. To that end, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. In addition, regarding the specific objectives recited above, it will be understood by those skilled in the art that one or more aspects of this invention can meet certain objectives, while one or more other aspects can meet certain other objectives. Each objective may not apply equally, in all its respects, to every aspect of this invention. As such, the objectives herein can be viewed in the alternative with respect to any one aspect of this invention.

BRIEF DESCRIPTION OF THE FIGURES

Various aspects and applications of the present invention will become apparent to the skilled artisan upon consideration of the brief description of figures and the detailed description of the present invention and its preferred embodiments that follows.

DETAILED DESCRIPTION OF THE PREFERRED EMBODIMENTS

Figure 1:
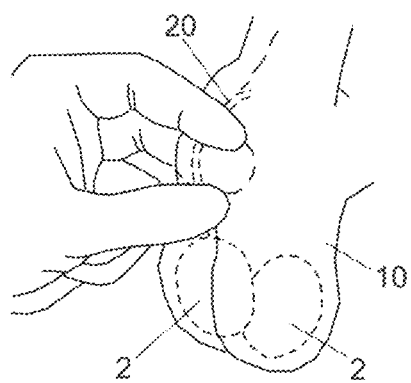
FIG. 1 depicts a first step in a prior art No Scalpel Vasectomy (NSV) procedure in which a vas duct is located in a fold of scrotal tissue.

Before the present materials and methods are described, it is to be understood that this invention is not limited to the specific devices, systems, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

All publications mentioned herein are incorporated herein by reference in their entirety. However, nothing herein should be construed as an admission that the invention is not entitled to antedate such disclosure by virtue of prior invention.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

As used herein, the noted directional terms relate to a human body in a standing position. For instance, "up" refers to the direction of the head, "down" refers to the direction of the feet. Likewise, herein, the "vertical" direction is parallel to the axis of the body and the "horizontal" direction is parallel to the floor. In a similar fashion, the term "lateral" refers to the direction extending away from the center of the body whereas "medial" refers to a direction extending toward the center of the body.

In the context of the present invention, the term "proximal" refers to that end or portion of a device or instrument which is situated closest to the body of the subject when the device is in use. Accordingly, the proximal end of an excising clamp or bipolar electrosurgical device of the present invention includes the handle portions.

In the context of the present invention, the term "distal" refers to that end or portion of a device or instrument that is situated farthest away from the body of the subject when the device is in use. Accordingly, the distal end of an excising clamp of the present invention includes the jaw components. Likewise, the distal region of the vas sheath comprises the "back side" farthest away from the practitioner.

In the context of the present invention, the term "arcuate" is used herein to describe shapes forming or resembling an arch. It is used interchangeably with its synonym, arciform.

Reference is made herein to "an arcuate sealed area" that contains one or more portions of the vas duct and a portion of its surrounding sheath. This "arcuate" area is exemplary only and not meant to be limiting. The sealed area may have a variety of regular or irregular shapes. Any sealed area formed by bipolar jaws positioned distal to a clamp located on the vas duct within the sheath falls within the scope of this invention. The sealed region may be arcuate, linear, irregularly shaped, or a combination of linear and curvilinear segments.

In describing some embodiments of methods of the present invention reference is made to the placement of a clamp on the midline of a vas duct within a vas sheath. It will be understood that such placement is imprecise and the midline of the clamping surface need not be on the exact midline of the duct. So long as a portion of the clamping surface of the clamp is closed upon a middle portion of the vas duct while minimizing contact with the distal region of the sheath, the method falls within the scope of this invention. In other embodiments, a clamp is configured such that the distal clamping surfaces may be positioned distal to the vas duct within the vas sheath. In these embodiments the clamp distal portion and bipolar jaws of the sealing device are configured so as to minimize their effect on nerves located in the sheath distal to the vas duct and therefore fall within the scope of this invention.

In the context of present invention, the terms "coagulated" and "cauterized" are interchangably used to describe a treated area of tissue. As used herein, coagulated or cauterized tissue is tissue that through the application of RF energy and pressure has been dessicated and fused to eliminate the flow of blood or other fluids.

In the context of the present invention, the term "convex" refers to a surface or boundary that curves outward, as the exterior of a sphere. Conversely, the term "concave" refers to a surface or boundary that curves inward, as to the inner surface of a sphere, or is hollowed or rounded inward like the inside of a bowl. Herein, the area of unclamped vas tissue defined by the U-shaped jaws of the bipolar coagulating device and the arcuate area of clamped vas tissue contained therein is referred to as convex in shape.

In the context of the present invention, the terms "vas" and "vas deferens" are used interchangeably to refer to the coiled biological channel that conveys sperm from the epididymis to the ejaculatory duct and the urethra that is comprised of an inner tubular duct (i.e., the "vas duct") and an outer muscular sheath (i.e., the "vas sheath").

In the context of the present invention, the terms "duct", and "vas duct" are used interchangeably to refer to the interior channel of vas deferens that serves to as a conveyance for sperm. Likewise, the terms "sheath" and "vas sheath" are used interchangeably to refer to the amorphous muscular sheath that surrounds the vas duct and houses the bulk of the sensory nerves.

Clamping devices suitable for use in the vasectomy methods of the present invention are used solely to maintain the position of the vas duct in the vas sheath for subsequent occlusion of the duct. Because a clamping device may contact the jaws of a bipolar handpiece during use, in order to prevent shorting of the bipolar device these clamps are formed of a dielectric material, typically a polymer or ceramic, or are formed of a metallic material and are covered with a dielectric coating. Indeed, clamps having a wide variety of configurations may be used including standard metal ring forceps and tenaculums to which a non-conductive coating has been applied.

As noted above, the present invention is characterized by substantial advantages not found in conventional methods and devices. For example, bruising of nerves in the vas sheath is minimized, and those in the sealed region and closely adjacent thereto are destroyed or deadened by a process known as RF neurotomy so as to reduce the probability of post procedure pain. By avoiding direct dissection and resulting bleeding, the present invention is able to eliminate the risk for development of massive hematomas and swelling. In addition, the present invention allows for the separation of the vas duct in such a manner that it is virtually impossible for the ends of the vas deferens to contact each other and rejoin. Also, the vasectomy procedure of the present invention requires fewer steps than other current vasectomy techniques, thereby reducing opportunities for complications and medical errors. Furthermore, the inherent simplicity of the disclosed procedure and associated instruments simplifies training and allows clinicians with limited experience to master their use. Moreover, the procedures of the present invention reduce exposure to bodily fluids, which, in turn, reduces the risks of transmission of blood-borne diseases, such a HIV and Hepatitis, to performing clinicians.

Although methods and materials similar or equivalent to those described herein can be used in the practice or testing of embodiments of the present invention, the preferred methods, devices, and materials are depicted in the accompanying figures and described hereinafter. However, the embodiments described herein are merely intended to illustrate the principles of the invention. Those skilled in the art will recognize that variations and modifications may be made to the embodiments without changing the principles of the invention herein disclosed. Accordingly, the accompanying figures, described in detail below that depict aspects of the invention are in no way intended to limit the scope of the present invention.

Examples

Figure 2:
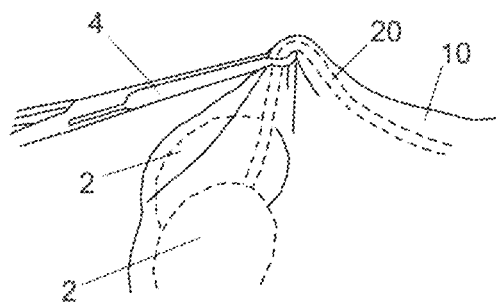
FIG. 2 depicts a subsequent step in the prior art NSV procedure in which the vas duct is isolated in a fold of scrotal tissue using a ringed clamp.
Figure 3:
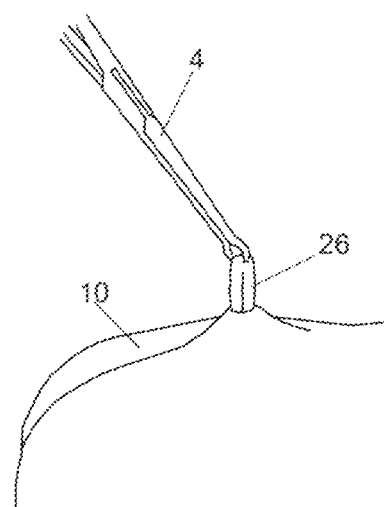
FIG. 3 depicts a subsequent step in the prior art NSV procedure in which an opening is formed in the scrotum and a portion of a vas duct in its surrounding sheath is extracted from the scrotum.
Figure 4:
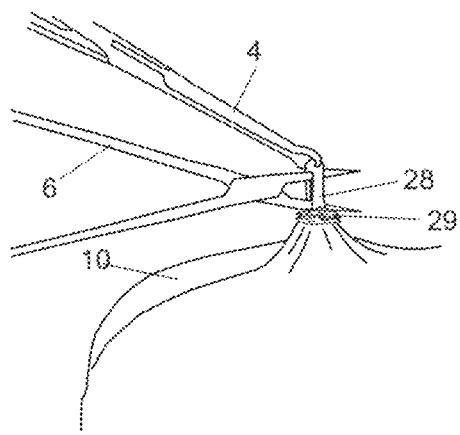
FIG. 4 depicts a subsequent step in the prior art NSV procedure in which the vas sheath is stripped back from the vas duct in preparation for occlusion.
Figure 5:
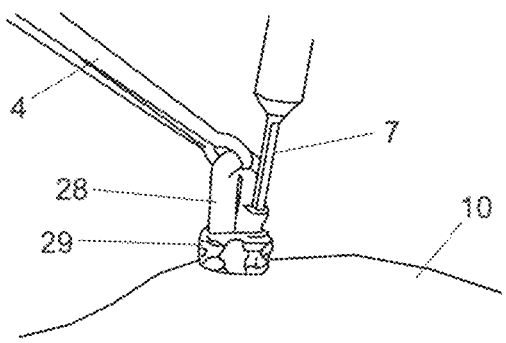
FIG. 5 depicts a subsequent step in the prior art NSV procedure in which a first side of the hemi-dissected vas duct is coagulated using a cautery.
Figure 6:
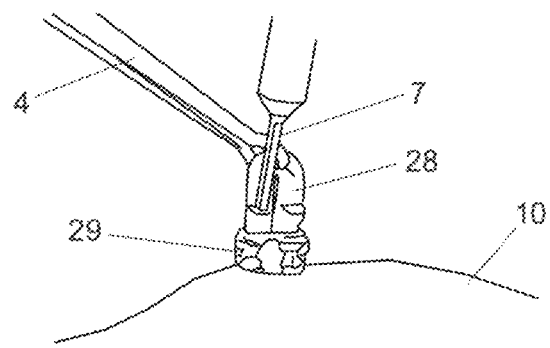
FIG. 6 depicts a subsequent step in the prior art NSV procedure in which a second side of the hemi-dissected vas duct is coagulated using a cautery.
Figure 7:
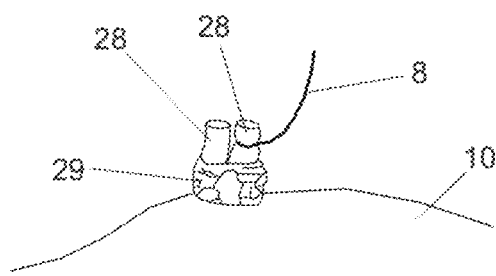
FIG. 7 depicts the vas duct after subsequent removal of the portion medial to the dissections in the prior art NSV procedure, with the end of the prostate leg ligated and the suture left untrimmed.
Figure 8:
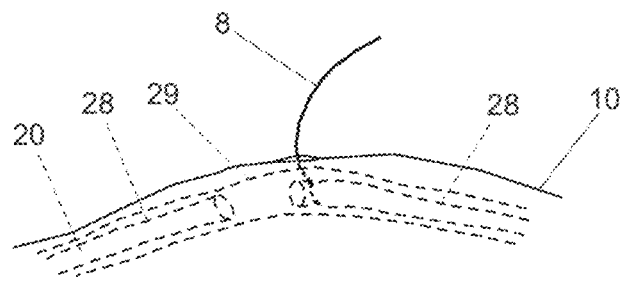
FIG. 8 depicts the site subsequent to FIG. 7, wherein the ends of the vas enclosed in the sheath are returned to the scrotum with the leg of the ligating suture extending from the puncture in the scrotum.
Figure 9:
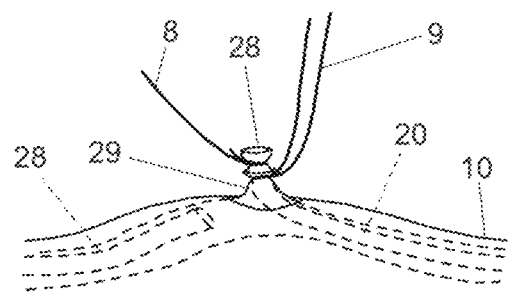
FIG. 9 depicts the site subsequently to FIG. 8, with the end of the prostate leg of the vas duct secured outside of the vas sheath so as to establish fascial interposition.
Figure 10:
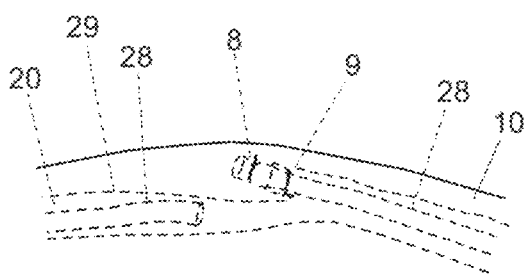
FIG. 10 depicts the site at completion of occlusion of the duct via the prior art NSV procedure in which the ends of the duct returned to the scrotum.

The most common method of vasectomy currently practiced is the No-Scalpel Vasectomy (NSV), a procedure in which the vas deferens is delivered from the scrotum via one or two openings in the scrotum formed by puncturing the scrotum and then expanding the opening(s). Steps of a typical prior-art NSV wherein a vas duct is occluded are depicted in FIGS. 1 through 10. In FIG. 1, a vas duct 20 is located in scrotum 10 using a standard technique. Thereafter, a local anesthetic is injected at the site. Duct 20 is then located in a fold of scrotum 10 using a ringed forceps 4 as shown in FIG. 2. The scrotum is then punctured using a dissecting forceps and the opening expanded sufficiently to allow the surgeon to deliver a portion 26 of vas duct 20 as depicted in FIG. 3. Dissecting forceps 6 are then used to puncture vas sheath 29 and then strip sheath 29 back to expose duct portion 28 as shown in FIG. 4. In FIGS. 5 and 6, duct portion 28 is hemi-dissected into abdominal and testicular portions, after which the distal element of an electrocautery 7 is inserted into the lumens of the respective portions and activated so as to form scar tissue in the lumens and thereby occlude them. Thereafter, as shown in FIG. 7, a suture 8 is applied to the abdominal leg of the separated duct portion 28. Next, vas sheath 29 with the testicular portion of separated duct 28 are drawn back into scrotum 10 with suture 8 extending through the opening in sheath 29 and the opening in scrotum 10 as shown in FIG. 8. In FIG. 9, suture 8 is used to draw duct 28 and sheath 29 out of scrotum 10, and to draw the abdominal side occluded end of duct 28 out of sheath 29, whereupon suture 10 is tied around a portion of sheath 28 and duct 29 as depicted in FIG. 9. Placing suture 9 in this manner permanently places a wall of sheath 29 between the divided occluded ends of duct 28 so as to provide an additional barrier to reuniting of the divided ends. FIG. 10 depicts the site with occluded, divided vas duct 20 returned to scrotum 10 with the duct ends being separated by fascial interpositioning.

As discussed elsewhere herein, the NSV procedure has multiple steps and requires extensive surgical skills. Completing the procedure generally requires twenty minutes or more. If the surgeon fails to notice and address any bleeders, hematomas may result. Because the scrotum is a flexible expandable vessel, these hematomas may become massive, resulting in pain and anxiety for the patient. In all cases, it is necessary for the patient to restrict activities following the procedure, frequently for a week or more.

The vas deferens, which is comprised of an inner duct and outer sheath, is innervated by a variety of different types of nerve ending. Adrenergic synapses are found in the smooth muscle layers. Cholinergic synapses and vasoactive intestinal peptide synapses are found in the connective tissue of the mucosa. Noradrenergic synapses may also be present in the vas deferens.

Figure 11:
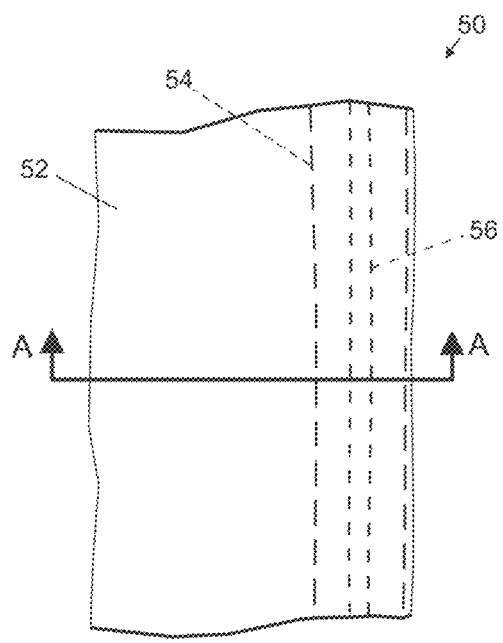
FIG. 11 is a diagrammatic plan view of a portion of a vas sheath and duct.
Figure 12:
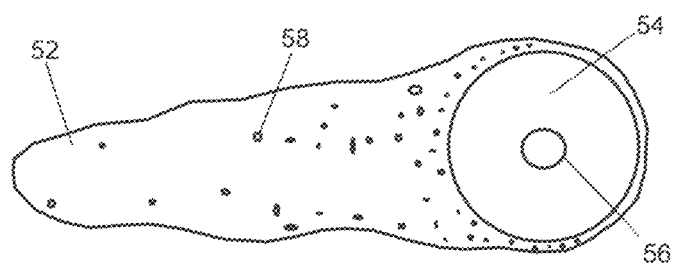
FIG. 12 is a sectional view of the objects of FIG. 11 at location A-A.

Referring now to FIGS. 11 and 12 depicting a short segment of vas 50, duct 54 has a lumen 56. Sheath 52 contains sensory nerves 58 primarily on the "back side" of the duct, distal to a clinician performing a vasectomy. When the vas sheath is "stripped back" as in FIG. 4, nerves 58 within sheath 52 may become bruised or otherwise injured. Following an NSV, patients experience varying levels of discomfort. These can range from mild transient discomfort that goes away in a few days or weeks, to severe chronic pain that may require surgical intervention, the latter being referred to as post vasectomy pain syndrome (PVPS). It is likely that bruising or other injury to sensory nerves 58 in sheath 52 is a significant contributing factor to post vasectomy pain. Indeed, one treatment for extreme cases of PSPV involves deadening of the nerves in the vas sheath in the region of the prior vasectomy.

Figure 13:
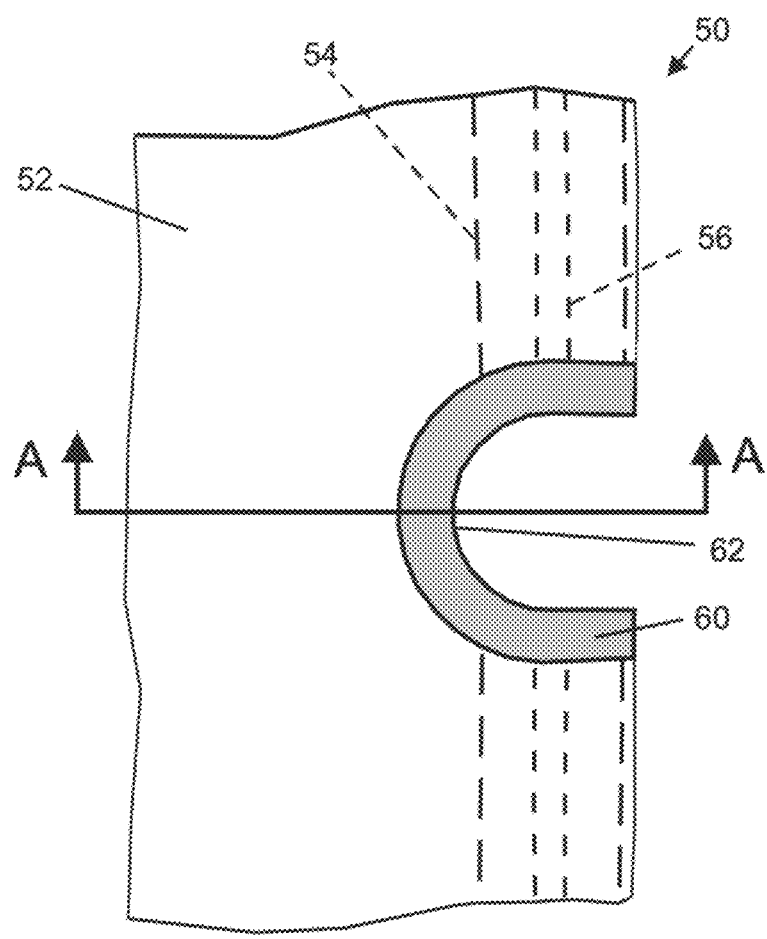
FIG. 13 is a diagrammatic plan view of a portion of a vas duct and sheath that have been sealed and the duct divided using methods of the present invention
Figure 14:
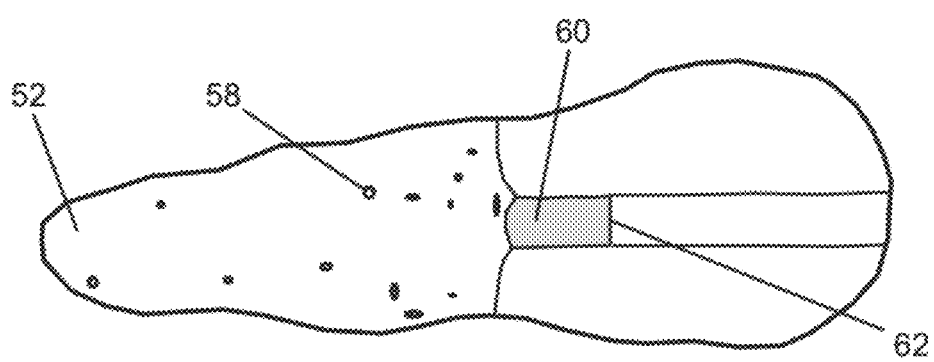
FIG. 14 is a sectional view of the objects of FIG. 13 at location A-A.
Figure 15:
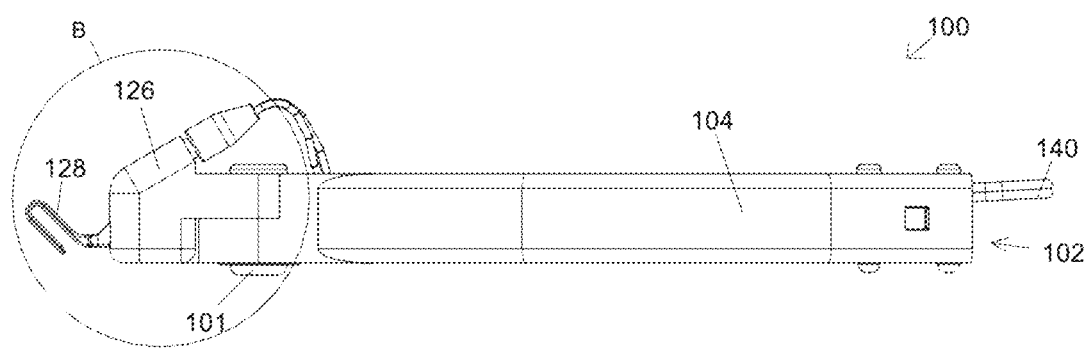
FIG. 15 is a plan view of a bipolar electrosurgical device for vasectomy methods of the present invention.
Figure 16:
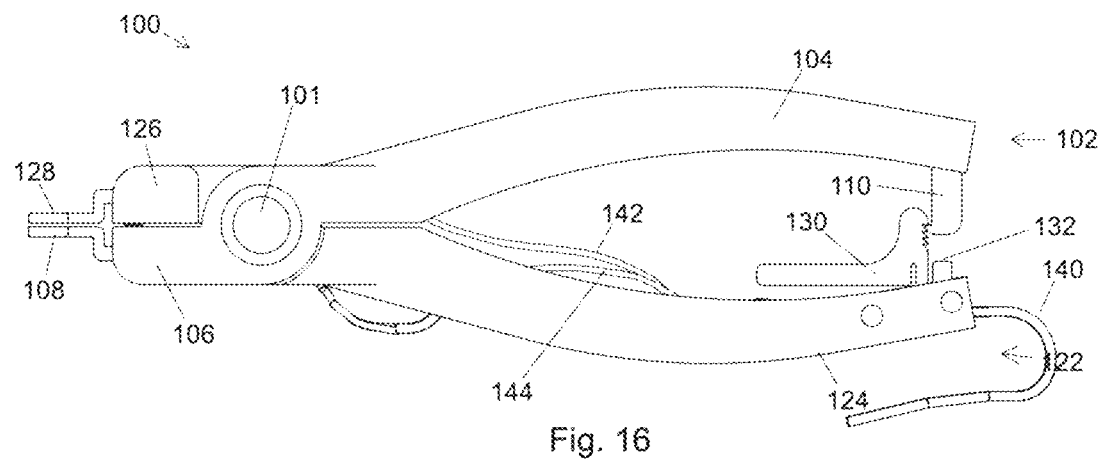
FIG. 16 is a side elevational view of the objects of FIG. 15.
Figure 17:
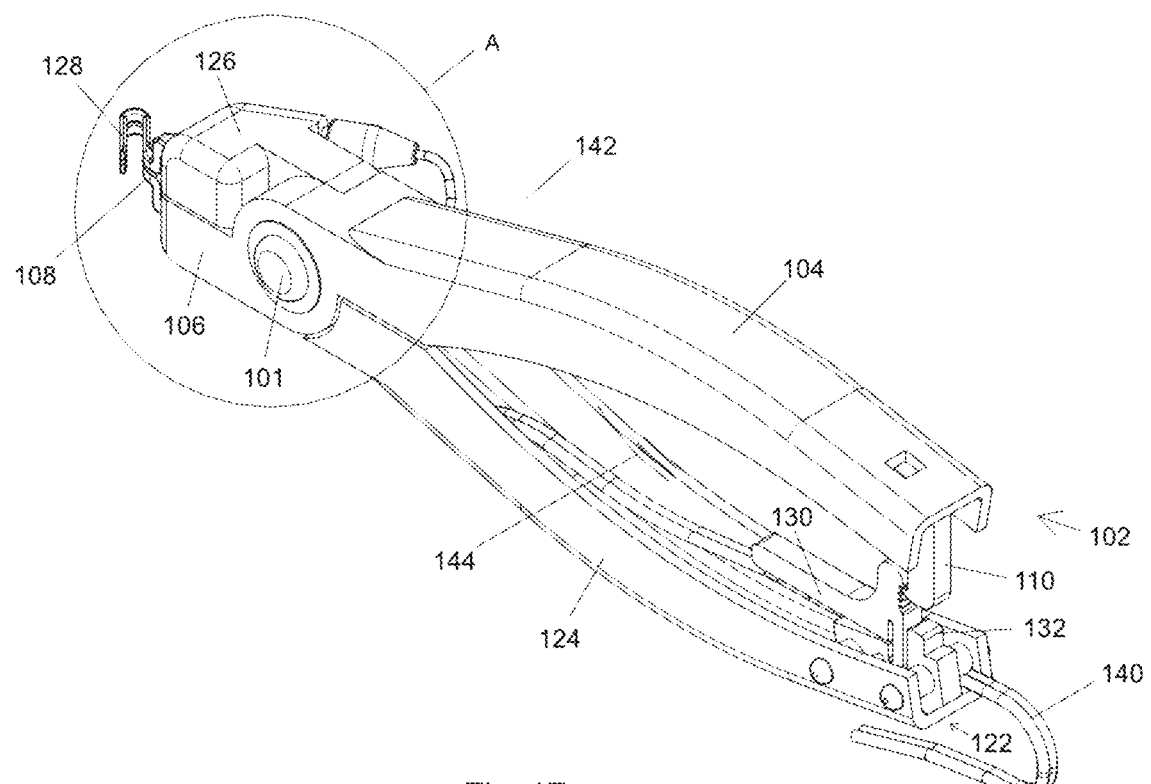
FIG. 17 is a perspective view of the objects of FIG. 15.

In the vasectomy procedures of the present invention, disruption of the nerves in proximity to the occlusion and dividing site is minimized. Referring now to FIGS. 13 and 14 depicting vas 50 at the completion of occluding and dividing duct 54 in accordance with the principle of the present invention, in arcuate region 60 tissue from duct 54 and sheath 52 is sealed by a bipolar RF sealing device. Thereafter tissue in region 62 is excised. Nerves 58 in region 60 are destroyed by the sealing process. Nerves 58 in close proximity to region 62 are deadened by the RF energy and resulting heat in a process commonly known as RF neurotomy. Nerves 58 that have been destroyed or deadened cannot cause post procedure pain. Bruising or other injury to nerves 58 is virtually eliminated.

The AUA Vasectomy Guidelines (American Urological Association Education and Research, Inc., Linthicum, Md. published in 2012) describe a vasectomy method used by Marie Stopes International (London, UK). In the document, the Marie Stopes method is referred to as "Non-Divisional Vasectomy with Extended Electrocautery". In this method, the vas is isolated and, without stripping the sheath back, a two to three centimeter portion of the duct is cauterized/vaporized from the proximal side, the adjacent proximal portion of the sheath being cauterized/vaporized along with the duct. The duct is not completely severed and some of the duct wall distal to the lumen remains—hence the designation as "non-divisional". The ducts of the vas are sealed by the heat of the adjacent cauterization. In a study cited in the guidelines, the failure rate for this non-divisional method was 0.64%. Because all of the work was done from the proximal side of the vas, the likelihood of bruising or injury to sensory nerves in the sheath is extremely low.

While the methods of the present invention parallel the Marie Stopes method in that sealing of the duct and sheath is accomplished from the proximal side, avoiding the stripping back of the sheath with its associated disruption of nerves distal to the duct, significant distinctions abound. For example, the seal created by the bipolar sealing device of the present invention is much more substantial than that created by simple cauterization/vaporization of the tissue by a single electrode in accordance with the teachings of Marie Stopes. To wit, in the methods of the present invention, sealing is accomplished by compression applied to the tissue and heating of the compressed tissue by RF energy. This method has been used for decades to seal blood vessels up to seven millimeters in diameter. In bench testing, seals formed in porcine vas duct using methods of the present invention did not fail when subjected to internal pressures in excess of 600 mm Hg.

Vasectomy techniques currently in use are considered to be "no scalpel" if the openings in the scrotum are not formed by incision using a cutting device, but rather by puncturing the scrotum and then using forceps to expand the opening by stretching the tissue. Many prospective vasectomy patients find the idea of an incision on their scrotum very intimidating. The "no scalpel" name attached to the current NSV method causes less patient anxiety. Many current NSV techniques create a single opening on the mid-line of the scrotum and both vas ducts are occluded through this opening, a way of further reducing patient anxiety.

A bipolar coagulating device (handpiece) 100 suitable for use in methods of the present invention is depicted in FIGS. 15 through 20 with the jaws in a first, clamped position. Handpiece 100 is substantially similar to the equivalent electrosurgical device described in Pannell '464, Pannell '615, and Van Wyk '831 and operates by an analogous procedure. To wit, bipolar handpiece 100 has an upper handle assembly 102 with a proximal handle portion 104 and a distal portion 106 wherein is mounted lower jaw 108. Handpiece 100 has a lower handle assembly 122 with a proximal handle portion 124 and a distal portion 126 wherein is mounted upper jaw 128. Upper handle assembly 102 and lower handle assembly 122 are rotatably joined by element 101. Lower handle assembly 122 has located adjacent to its proximal end ratchet element 130 that, in cooperation with downward extending proximal portion 110 of upper handle assembly 102 maintains the clamping force of jaws 108 and 128, portion 132 of ratchet element 130 limiting the interjaw force that can be applied. Bipolar cable 140 is connected at its proximal end to the bipolar outputs of a suitable electrosurgical generator, and at its distal end, via wires 142 and 144 to upper jaw 128 and lower jaw 108 respectively such that Radio Frequency (RF) energy from the generator is conducted to jaws 108 and 128 so as to coagulate tissue clamped therebetween. In a preferred embodiment, RF energy from the electrosurgical generator is modulated according to an algorithm in the generator for maximal coagulation of tissue between the jaws.

Figure 18:
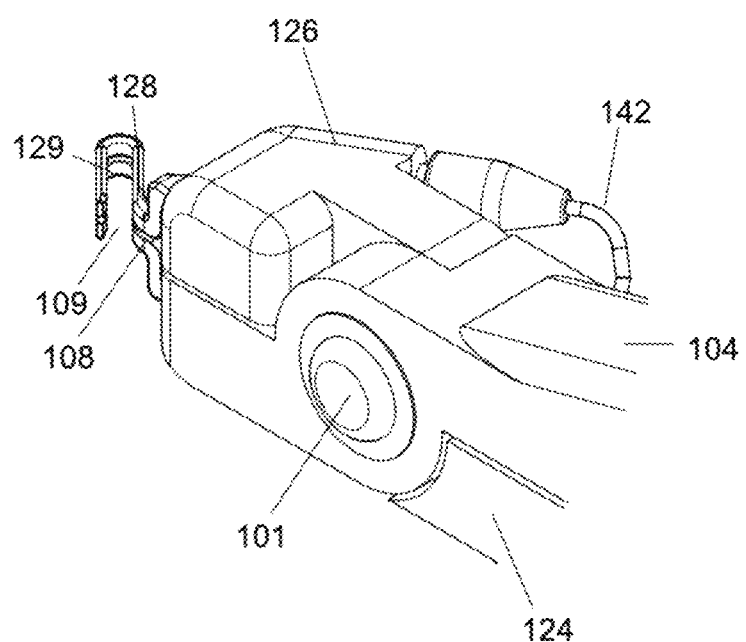
FIG. 18 is an expanded view of the objects of FIG. 17 at location A.
Figure 19:
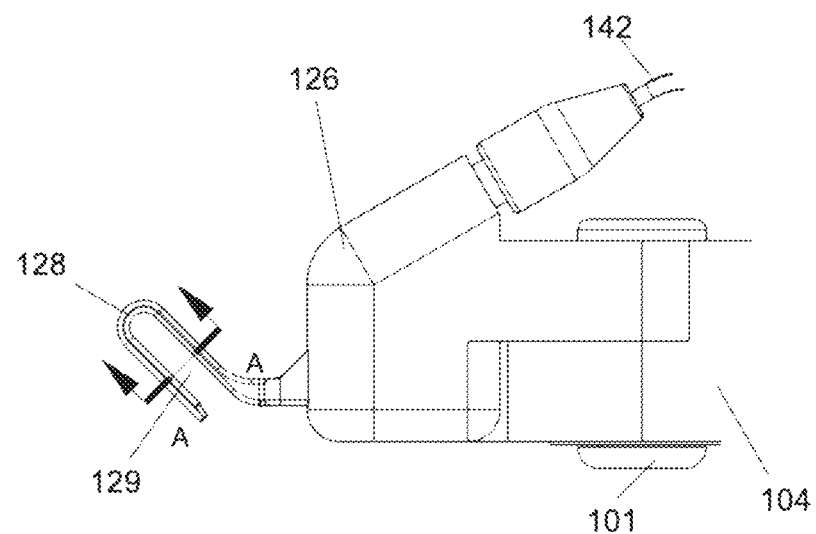
FIG. 19 is an expanded view of the objects of FIG. 18 at location A.
Figure 20:
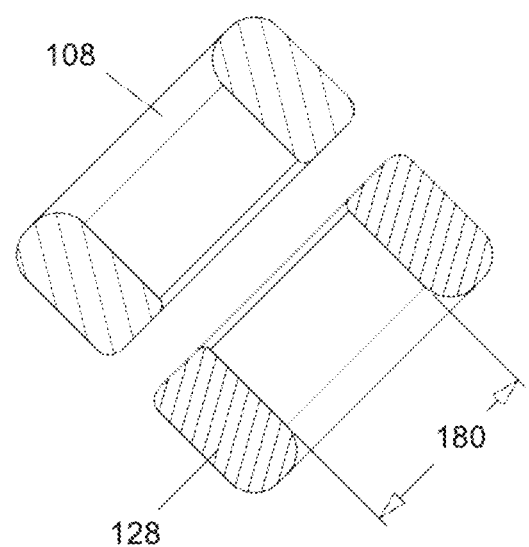
FIG. 20 is an expanded sectional view of the objects of FIG. 19 at location A-A.

As best seen in the close-up views of FIGS. 18-20, upper 128 and lower 108 jaws are mirror images, each including a proximal portion that attaches to the distal end of the handpiece and a distal portion that is angularly off-set from the longitudinal axis defined by the handpiece, preferably disposed at an angle of about 45 degrees. The angular offset affords the surgeon better visibility and access to the target surgical site. As best seen in FIG. 19, upper jaw 128 has a "U" shape with a central slot 129 of width 180, with lower jaw 108 having a corresponding shape so that tissue may be clamped between the U-shaped jaw portions of jaws 108 and 128.

Referring now to FIG. 20, the U-portions of jaws 108 and 128 preferably have radiused outer circumferential portions adjacent to their clamping surfaces to prevent cutting of tissue clamped between jaws 108 and 128. In a preferred embodiment, each offset central slot defined by each "U-shaped" distal portion is approximately 1-3 mm in width.

Figure 21:
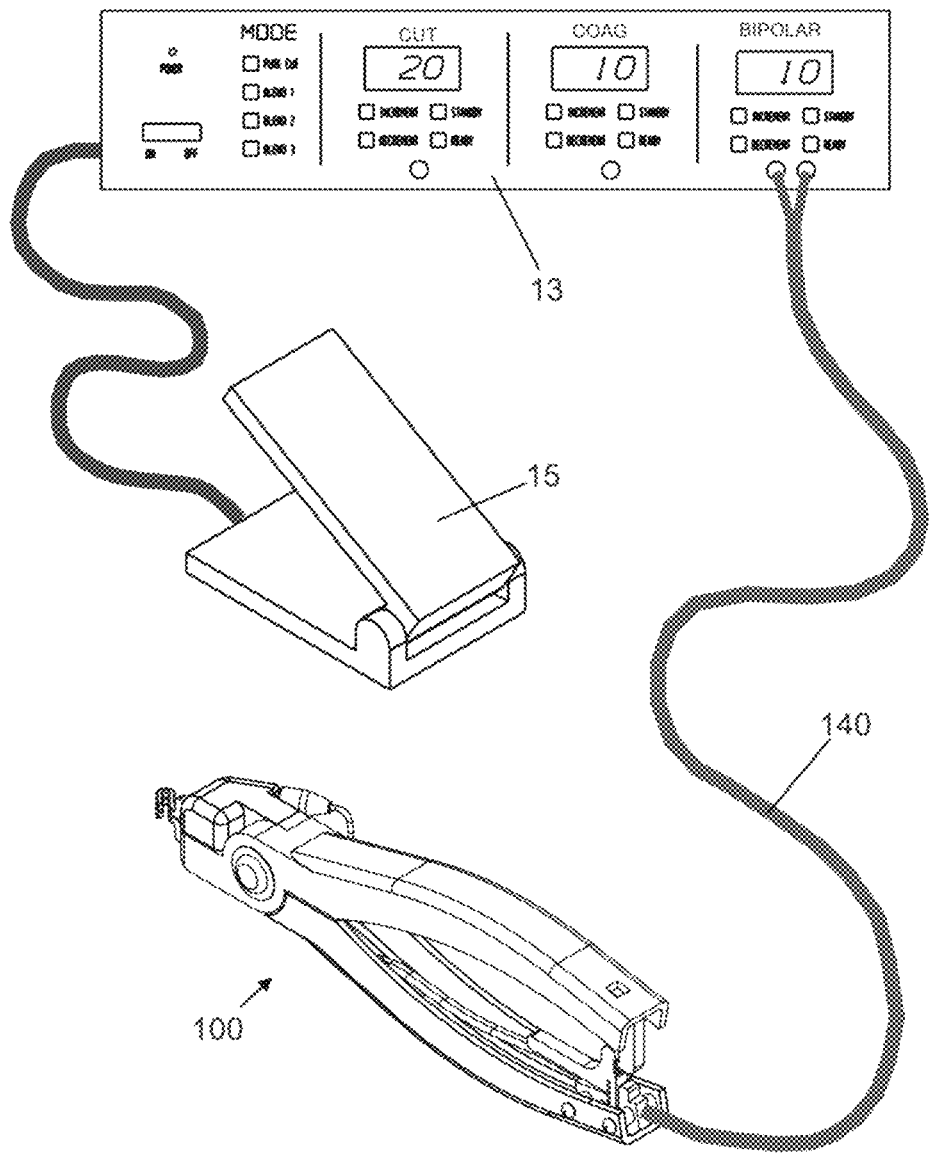
FIG. 21 depicts a bipolar sealing device used in vasectomy methods of the present invention connected to an electrosurgical generator in preparation for use, and the footpedal used for generator activation.
Figure 22:
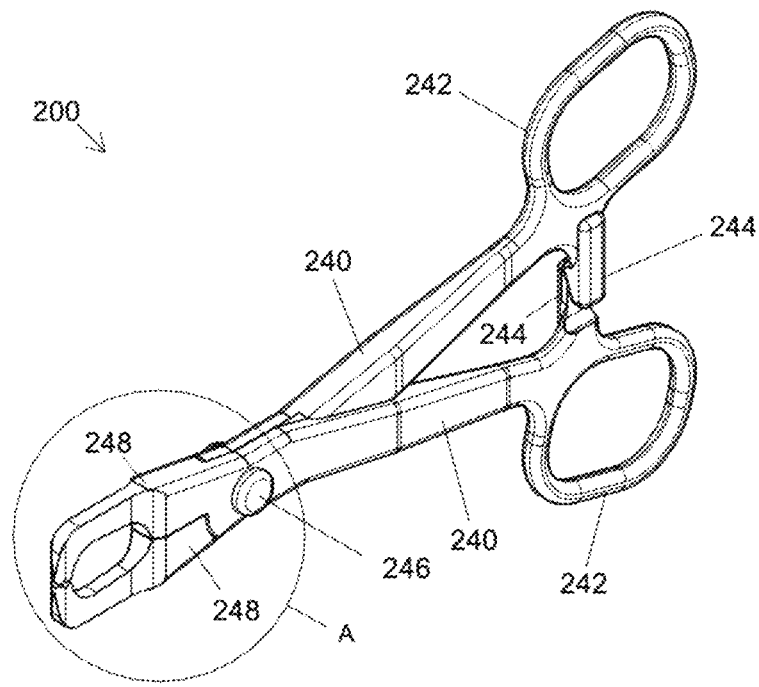
FIG. 22 is a perspective view of a non-conductive clamp for use in vasectomy methods of the present invention.
Figure 23:
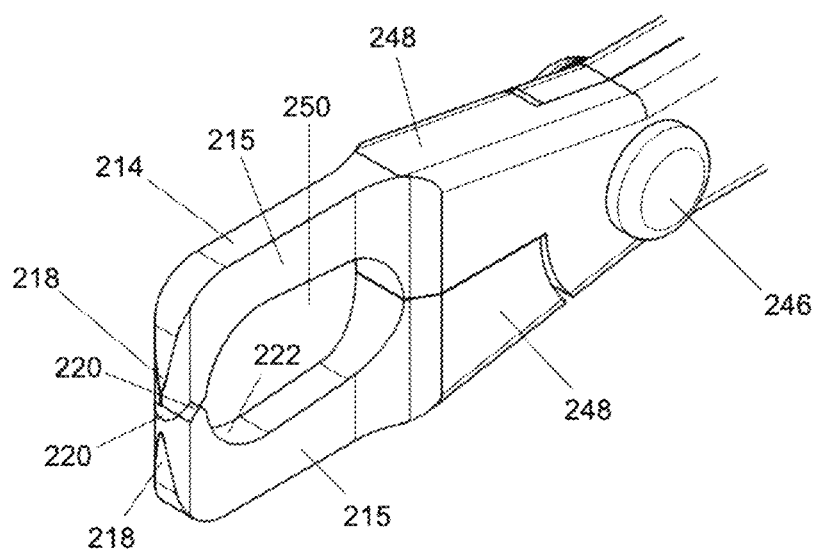
FIG. 23 is an expanded view of the objects of FIG. 22 at location A.
Figure 24:
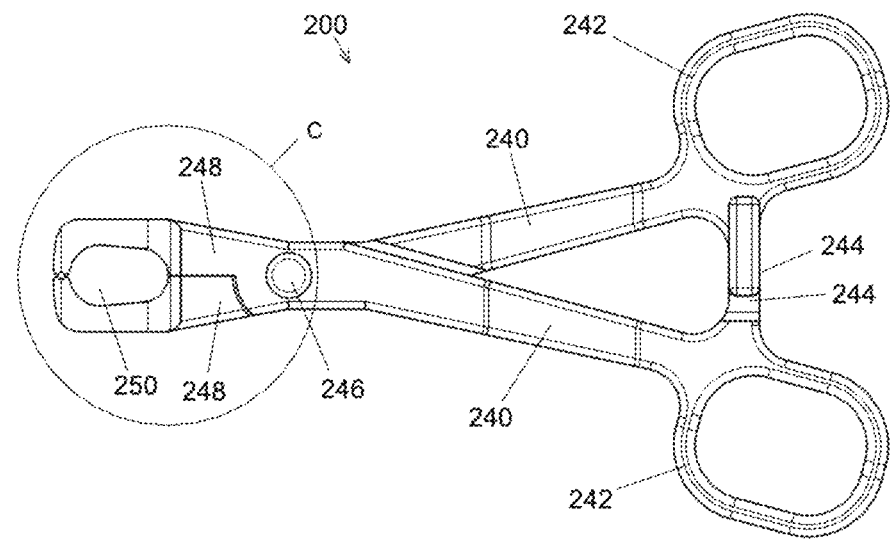
FIG. 24 is a side elevational view of the objects of FIG. 22.
Figure 25:
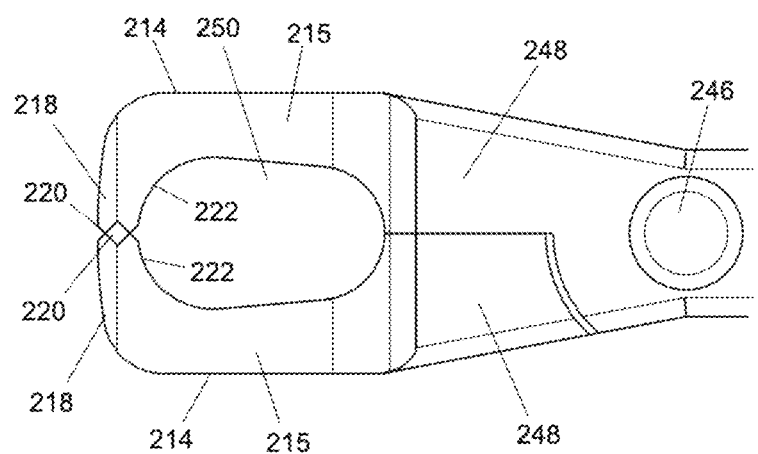
FIG. 25 is an expanded view of the objects of FIG. 24 at location C.
Figure 26:
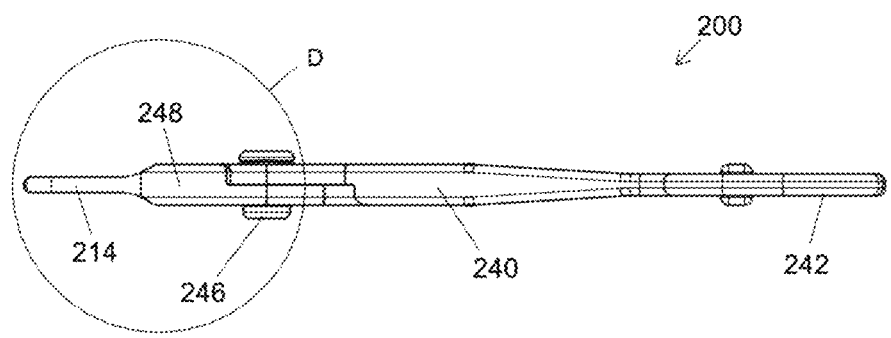
FIG. 26 is a plan view of the objects of FIG. 22.
Figure 27:
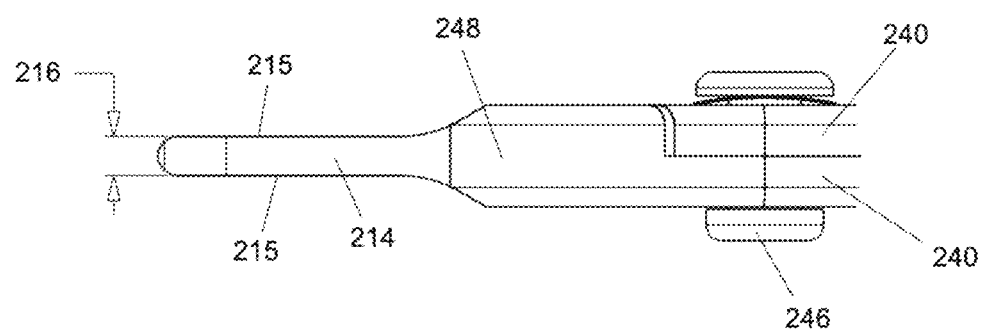
FIG. 27 is an expanded view of the objects of FIG. 26 at location D.

FIG. 21 depicts bipolar coagulating device 100 connected by cable 140 to the bipolar outputs of electrosurgical generator 13 that is suitable for use in connection with the inventive methods. In the depicted preferred embodiment, generator 13 is activated by foot pedal 15. While not shown, it is understood that electrosurgical generator may be powered by alternating current, for example, via a conventional wall socket, or alternatively may be powered by direct current, for example, by means of an included rechargeable power source. Generator 13 depicted is a general purpose generator of the type found in all operating rooms.

In other embodiments, generator 13 may take the form of a special purpose generator configured exclusively for use with bipolar coagulating device 100. In these embodiments, generator 13 is configured to provide the RF energy as a series of pulses, and further has the ability to monitor the impedance of tissue clamped between mating jaws 108 and 128 during sealing. In certain embodiments, the generator may give an audible signal to the clinician or cease activation when a complete seal is detected based on the impedance of tissue between the jaws sensed by the generator. In some embodiments, the power level of the generator output may be optimized based on the initial impedance of the tissue between jaws 108 and 128 of handpiece 100.

In FIGS. 22 through 27, clamp 200 is formed of elements 240 having proximal portions that form finger holes 242, and whereon are formed ratchet portions 244. Elements 240 are pivotably joined by element 246. Distal to element 246, distal portions 248 of elements 240 have a distal-most portion 214 of width 216 (FIG. 27) that is less than width 180 of slots 129 and 109 of jaws 128 and 108 respectively (see FIG. 20). Distal-most portions 214 have at their distal ends jaw portions 218 with vertically opposed, planar jaw faces 220. Distal-most portions 214 have laterally opposed surfaces 215, and surfaces 222 that are perpendicular to surfaces 215, and that together define distal opening 250 of clamp 200. Clamp 200 may be made from a suitable dielectric material or from a metallic material with the distal portions 714 coated with a suitable dielectric coating so as to prevent shorting of bipolar handpiece 100 during use.

Figure 28:
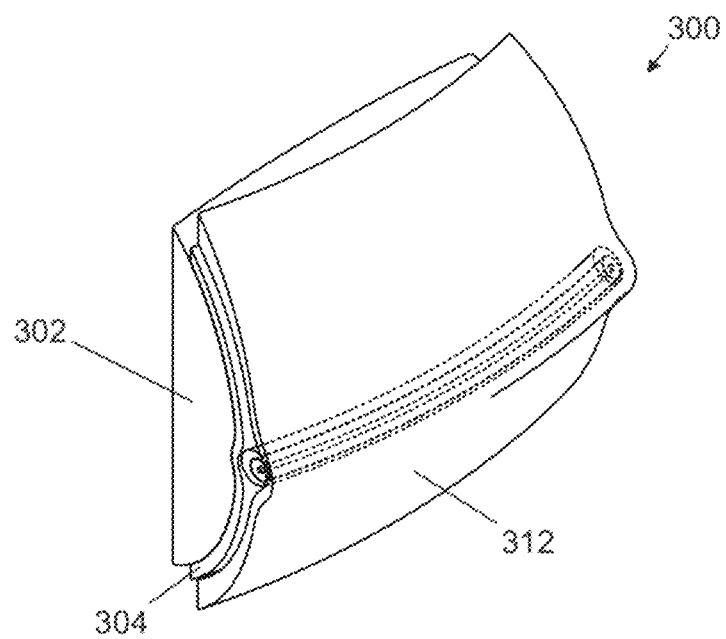
FIG. 28 is a perspective diagrammatic view of a portion of a scrotum with the vas positioned adjacent to the outer scrotal wall in preparation for a vasectomy using methods of the present invention.
Figure 29A:
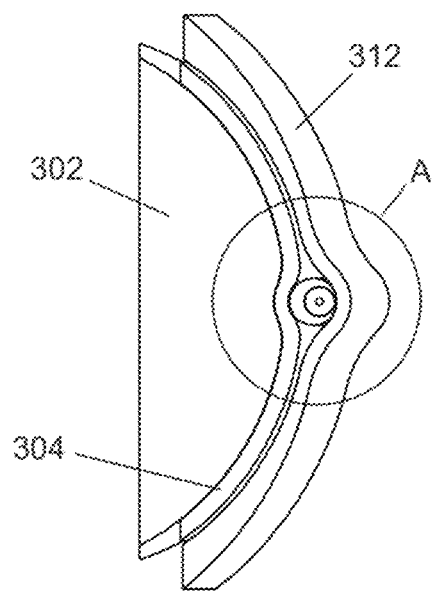
FIG. 29A is a side elevational view of the objects of FIG. 28.
Figure 29B:
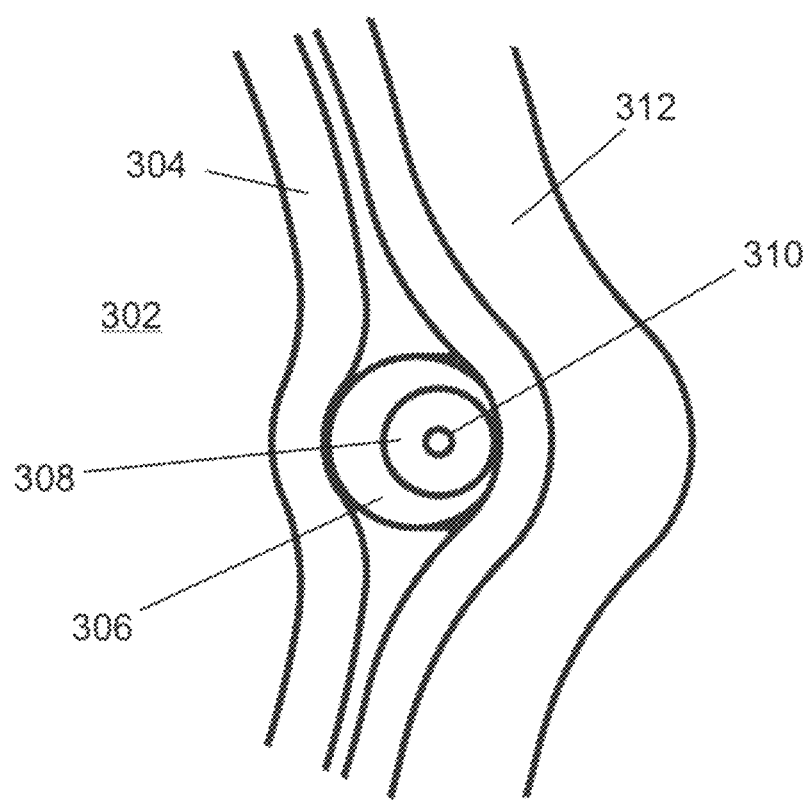
FIG. 29B is an expanded view of the objects of FIG. 29A at location A.
Figure 30:
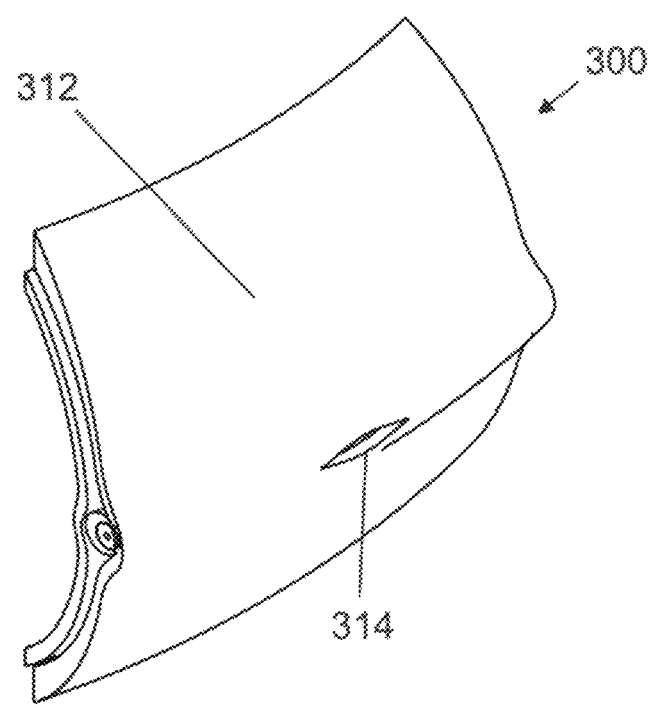
FIG. 30 is a perspective view of the scrotal portion of FIG. 28 wherein an opening has been formed in the outer scrotal wall in a first step in a vasectomy of the present invention.
Figure 31:
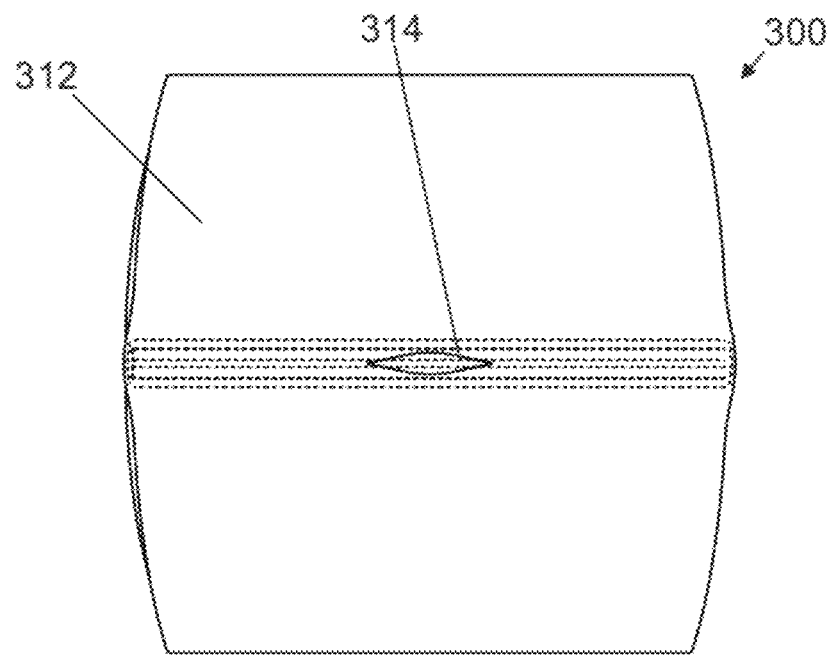
FIG. 31 is a side elevational view of the objects of FIG. 30.
Figure 32:
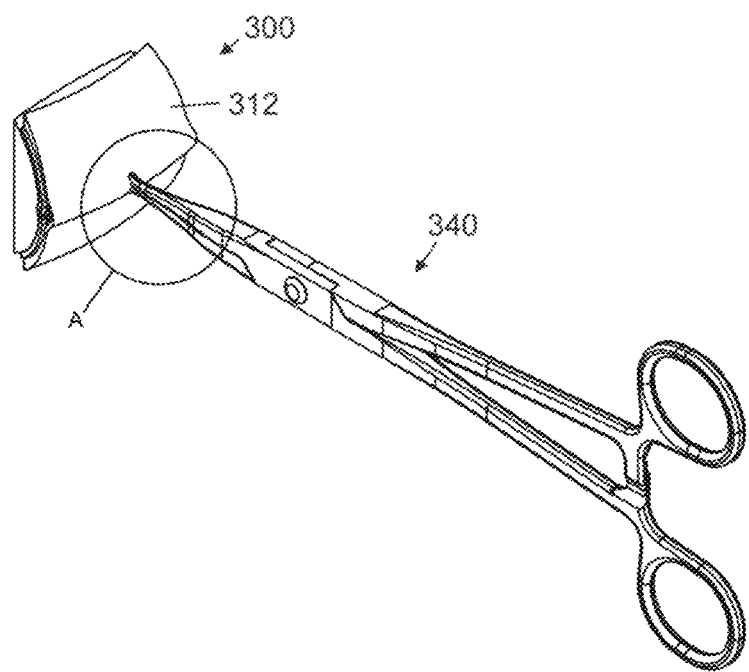
FIG. 32 is a perspective view of the scrotal portion of FIG. 30 depicting a second step in a vasectomy of the present invention wherein a standard vasectomy ring clamp is inserted into the opening so as to grasp the vas sheath containing the vas duct in preparation for bringing the vas out of the scrotum.
Figure 33:
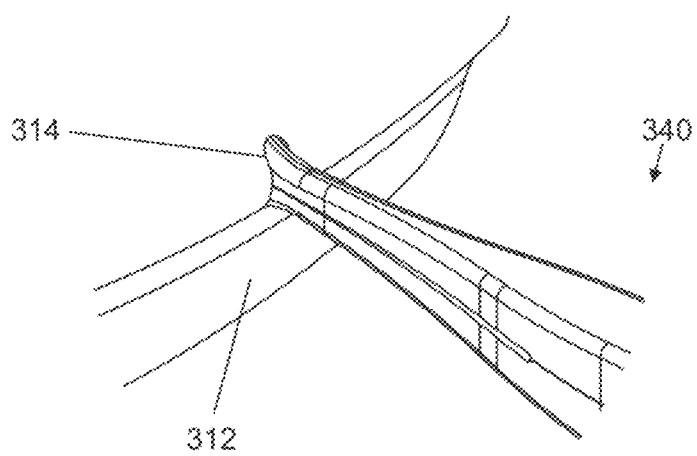
FIG. 33 is an expanded view of the objects of FIG. 32 at location A.
Figure 34:
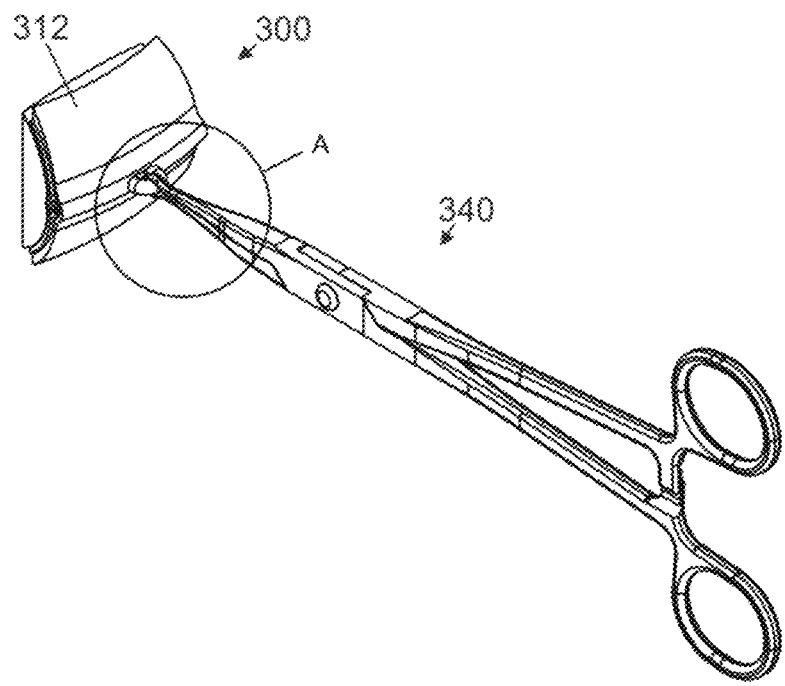
FIG. 34 depicts the objects of FIG. 32 wherein the vas has been delivered (isolated) from the scrotum in a third step of a vasectomy using methods of the present invention.
Figure 35:
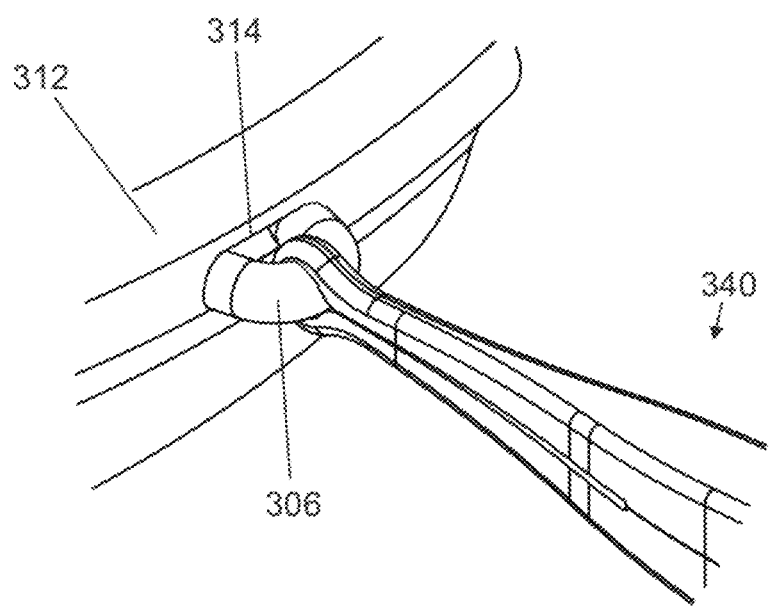
FIG. 35 is an expanded view of the objects of FIG. 34 at location A.
Figure 36:
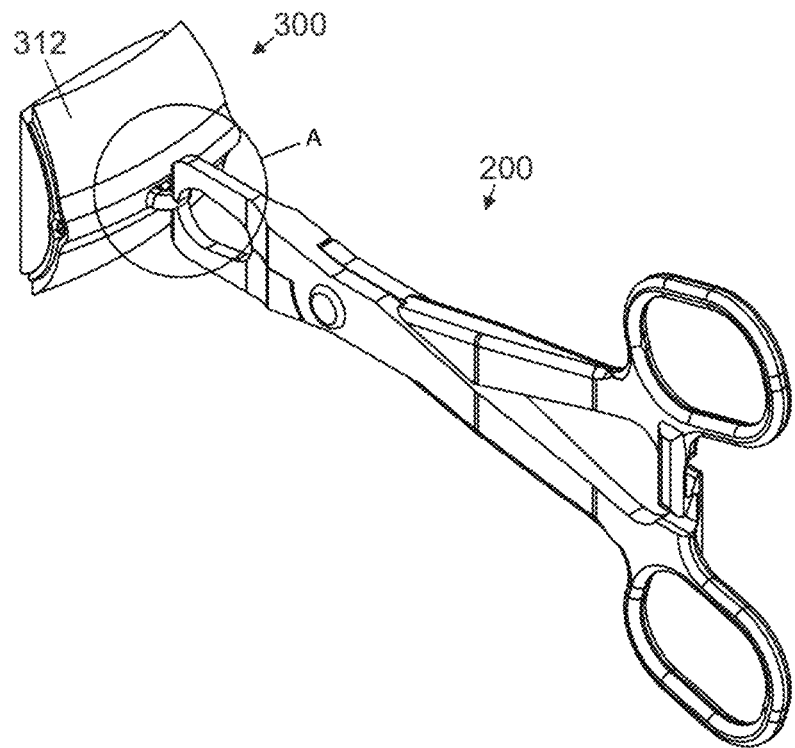
FIG. 36 is a perspective view of a fourth step in a vasectomy of the present invention wherein the vasectomy ring clamp has been replaced by a non-conductive clamp.
Figure 37:
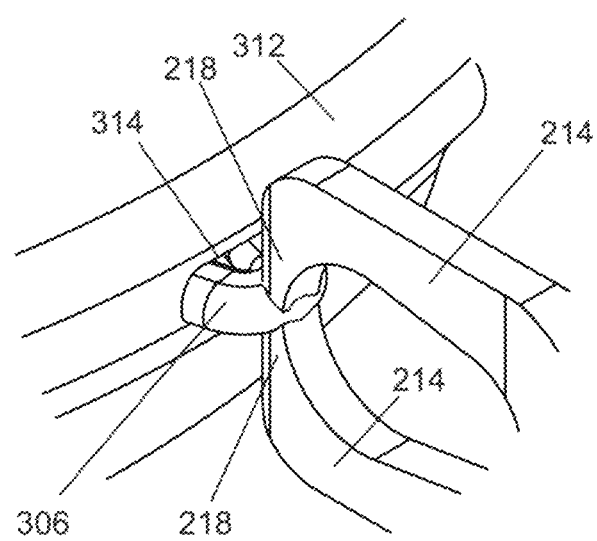
FIG. 37 is an expanded view of the objects of FIG. 36 at location A.
Figure 38:
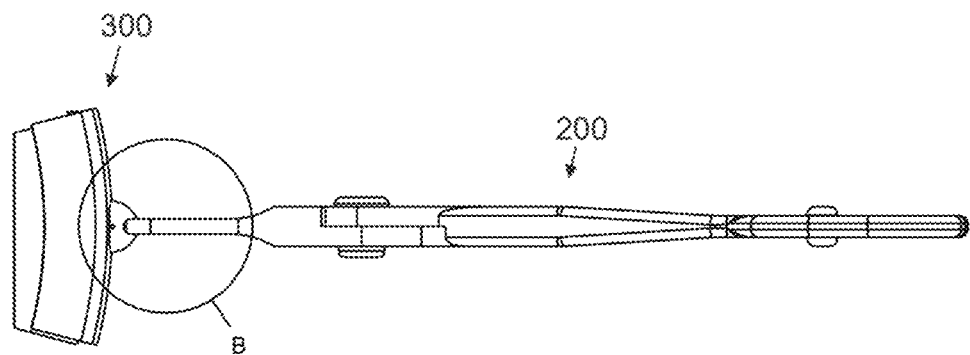
FIG. 38 is a plan view of the objects of FIG. 36.
Figure 39:
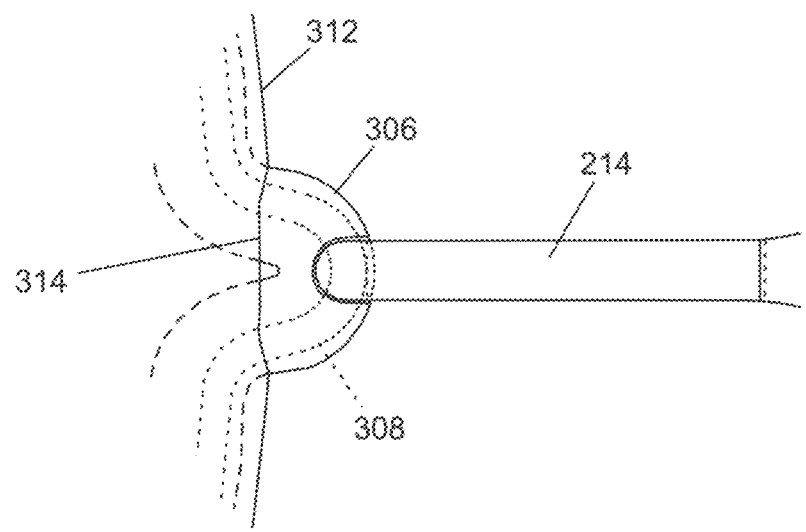
FIG. 39 is an expanded view of the objects of FIG. 38 at location A.
Figure 40:
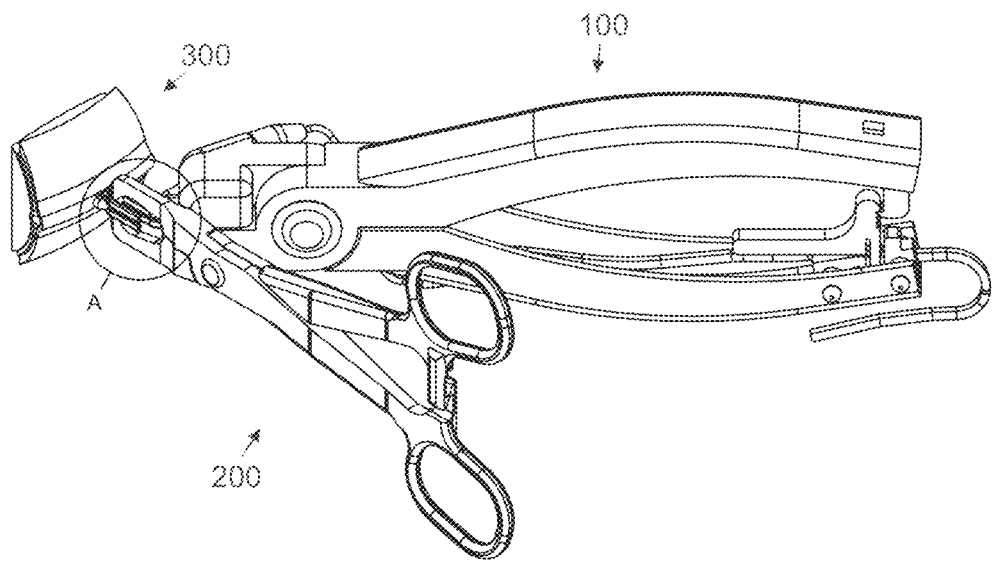
FIG. 40 is a perspective view of a fifth step of vasectomy using methods of the present invention in which the jaws of an RF bipolar sealing device are positioned around the previously placed clamp, closed on the vas, and energized so as to seal the tissue compressed between the jaws.
Figure 41:
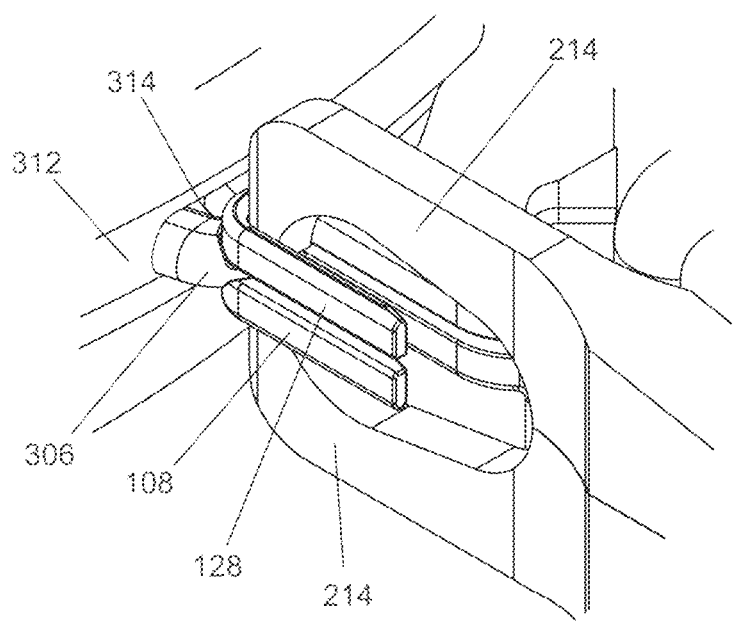
FIG. 41 is an expanded view of the objects of FIG. 40 at location A.
Figure 42:
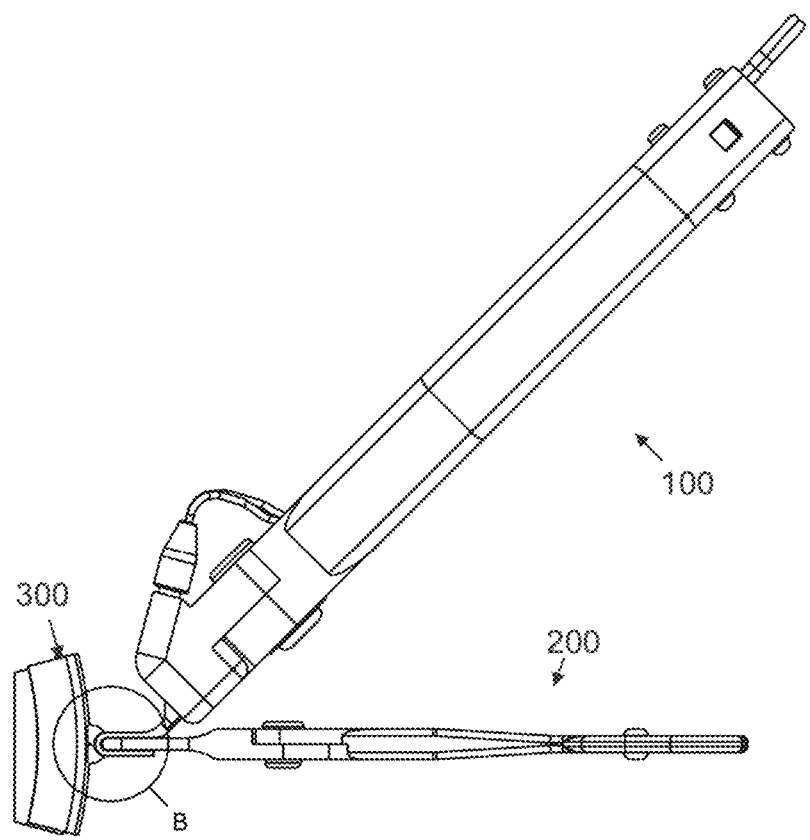
FIG. 42 is a plan view of the objects of FIG. 40.
Figure 43:
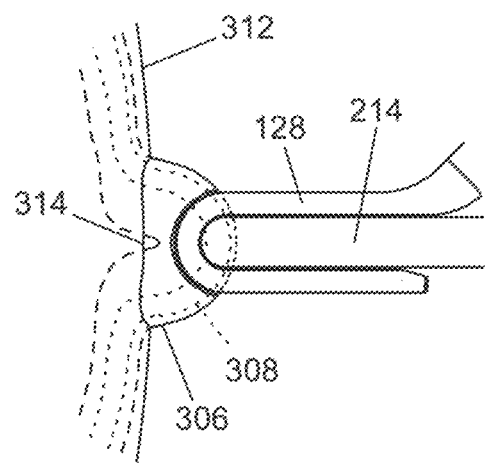
FIG. 43 is an expanded view of the objects of FIG. 42 at location B.

Hereafter a vasectomy performed using methods of the present invention will be described. The methods of the present invention begin in the same manner as a typical NSV, such as described in Van Wyk '831, with a vas located in the scrotum and brought to a location beneath the scrotal skin as depicted in FIGS. 28-29B depicting portion 300 of a scrotum. Referring to the Figures, duct 308 with lumen 310 is surrounded by sheath 306. Hand portion 302 forces inner scrotum wall 304 outward toward outer scrotum wall 312, trapping duct 308 and sheath 306 therebetween so as to position duct 308 and sheath 306 for a vasectomy of the present invention. As shown in FIGS. 30 and 31, opening 314 is formed in outer scrotum wall 312 to allow isolation of sheath 306 and duct 308. A standard vasectomy ring clamp (ring forceps) 340 is inserted into opening 314 to grasp duct 308 and sheath 306 as depicted in FIGS. 32 and 33. Thereafter, sheath 306 and duct 308 are isolated outside the scrotum (see FIGS. 34 and 35). Clamp 200 is then applied as shown in FIGS. 36-39, with distal clamping portions 218 of clamp 200 being centered on duct 310, thereby minimizing contact with the distal wall of the vas sheath and the sensory nerves embedded therein. After clamp 200 is in position, ring clamp 340 is removed.

Referring now to FIGS. 40-43, mating jaws 108 and 128 of handpiece 100 are positioned around clamping portions 218 of clamp 200, the clamping portions 218 of clamp 200 ensuring accurate positioning of jaws 108 and 128 so as to minimize the size of the sealed/coagulated region. Jaws 108 and 128 are then closed on portions of duct 208 and sheath 206 between the clamping surfaces of jaws 108 and 128 so as to apply a compressive force. Thereafter, generator 13 (see FIG. 21) is activated, thereby supplying RF energy to jaws 108 and 128. RF energy passing between jaws 108 and 128 heats adjacent portions of duct 208 and sheath 206 to a degree sufficient to cause desiccation and remodeling of collagen and elastin in the tissues so as to thereby form a seal. When sealing is complete, the flow of RF energy from generator 13 is terminated. Clamp 200 is then removed.

Figure 44:
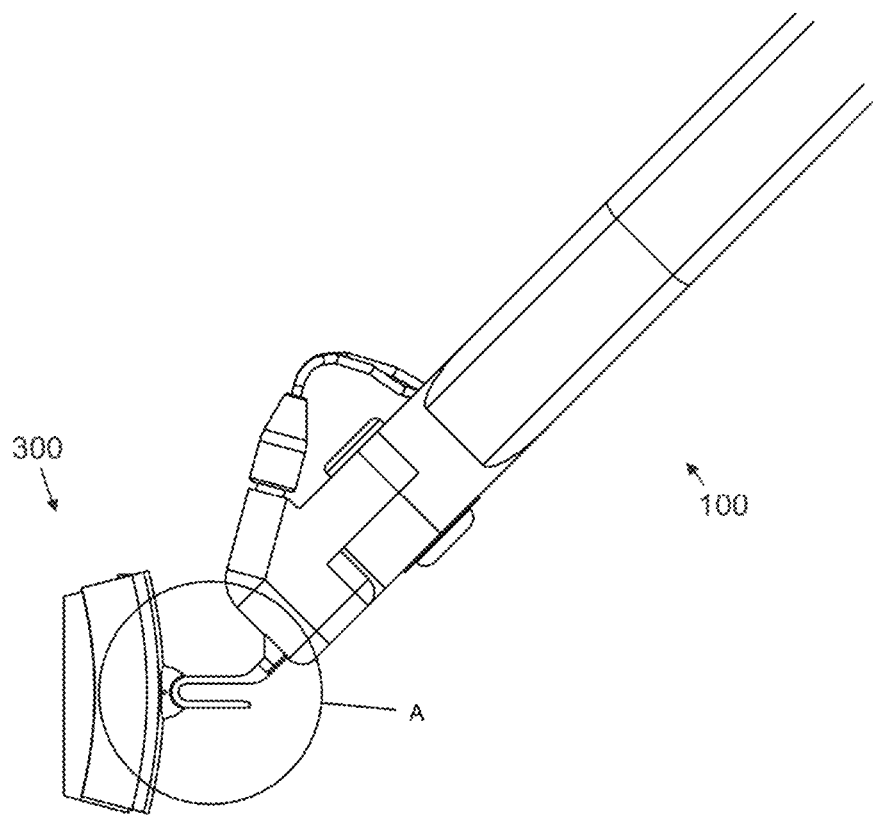
FIG. 44 depicts a sixth step of a vasectomy method of the present invention in which the non-conductive clamp has been removed, and the central uncoagulated tissue portion excised.
Figure 45:
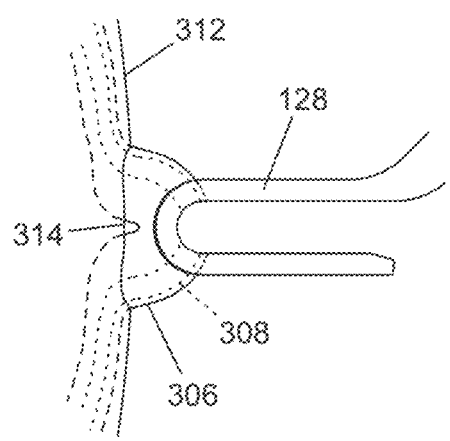
FIG. 45 is an expanded view of the objects of FIG. 44 at location A.
Figure 46:
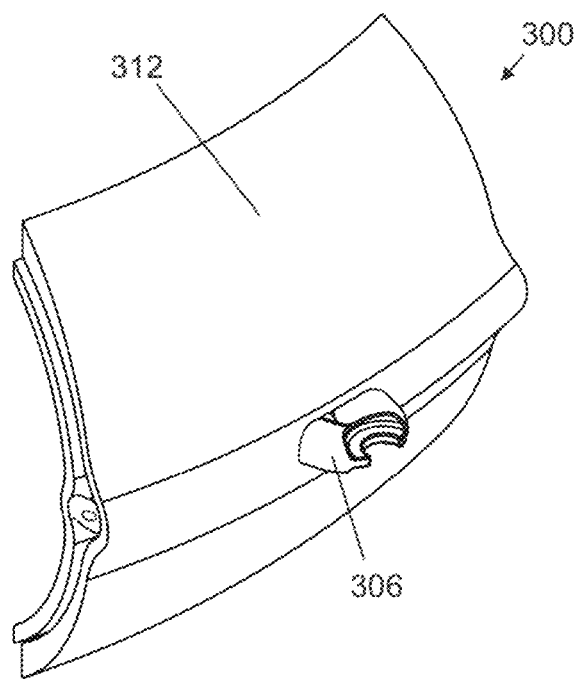
FIG. 46 is a perspective view of the vas at the completion of sealing and dividing steps of a vasectomy method of the present invention.
Figure 47:
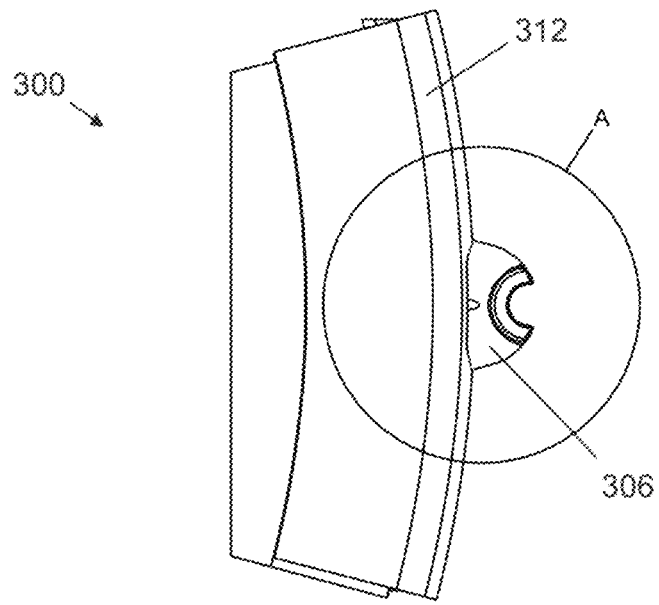
FIG. 47 is a plan view of the objects of FIG. 46.
Figure 48:
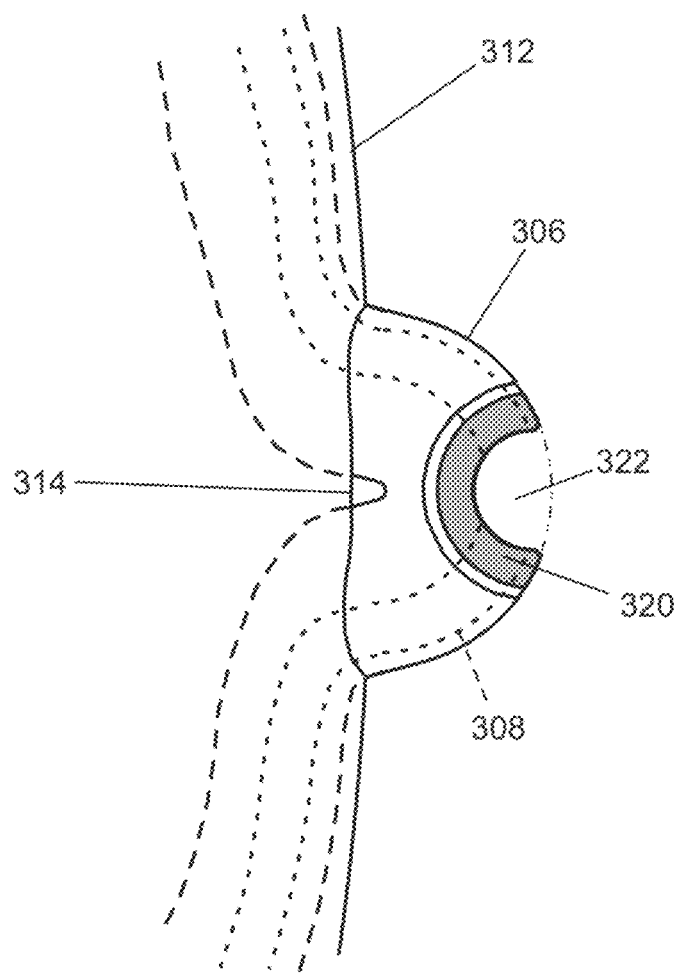
FIG. 48 is an expanded view of the objects of FIG. 47 at location A.

In certain embodiments, clamp 200 is not released prior to removal and tissue trapped between clamping portions 218 of clamp 200 is excised with the removal of clamp 200. In other embodiments, clamp 200 is released prior to removal from the site and uncoagulated tissue remaining within slot 129 of jaw 128 is excised using another instrument. In either case, clamp 200 is removed and tissue remaining in slot 129 of jaw 128 is excised while handpiece 100 remains in position with jaws 108 and 128 protecting the sealed region as shown in FIGS. 44 and 45. Handpiece 100 is then released and removed. FIGS. 46-48 depict the site at completion of occlusion and dividing of duct 308 in accordance with the principles of the present invention. Arcuate sealed region 320 contains two ends of duct 308 and portions of sheath 306 surrounding excised region 322. Duct 308 is thereby sealed and divided as recommended in the AUA Vasectomy Guidelines. Thereafter, sheath 306 and divided duct 310 are returned to the scrotum. The procedure is repeated on the second duct. This may be accomplished by forming a second opening 314 to access the second duct, or both ducts may be occluded as described through a single mid-line opening 314.

Referring again to FIGS. 1-10, current NSV techniques are not only prone to causing bruising and injuries to nerves resulting in post procedure pain, but they also involve multiple steps that require surgical skills. As such, extensive training is required to master the technique. In contrast, in vasectomy methods of the present invention, the prior art steps depicted in FIGS. 4 through 9, i.e., those that require surgical skills, are replaced by the steps depicted in FIGS. 36-45, i.e., steps that do not require surgical skills. In this manner, vasectomy methods of the present invention may be taught to non-surgeons and quickly mastered. This is of particular value in low resource regions wherein a lack of surgeons limits the availability of vasectomy as a tool for family planning. Using methods of the present invention, a vasectomy can be completed in a much shorter time and with reduced opportunities for hematomas and other complications compared to present NSV methods.

In one embodiment of the vasectomy method of the present invention previously herein described, the uncoagulated tissue portion between clamping portions 218 of clamp 200 is excised after sealing was completed as shown in FIGS. 44 and 45. However, in other alternative embodiments of the present invention, the practioner may opt not to excise the uncoagulated tissue but rather to leave it in place to slough off in due course. In particular, because the region is circumscribed by sealed region 320, tissue within the region has no blood supply and will necrose and be absorbed by the body over time, thereby dividing vas duct 308.

In the vasectomy procedure depicted in FIGS. 32-35, a standard vasectomy ring clamp 340 is used to isolate the vas and bring it out of the scrotum. Thereafter, as shown in FIGS. 36 to 39, ring clamp 340 is replaced by non-conductive clamp 200 with clamp 200 being positioned on the midline of duct 308. However, in other embodiments of the present invention, a metal clamp with an insulated distal portion may be used to isolate and deliver the vas.

Figure 49:
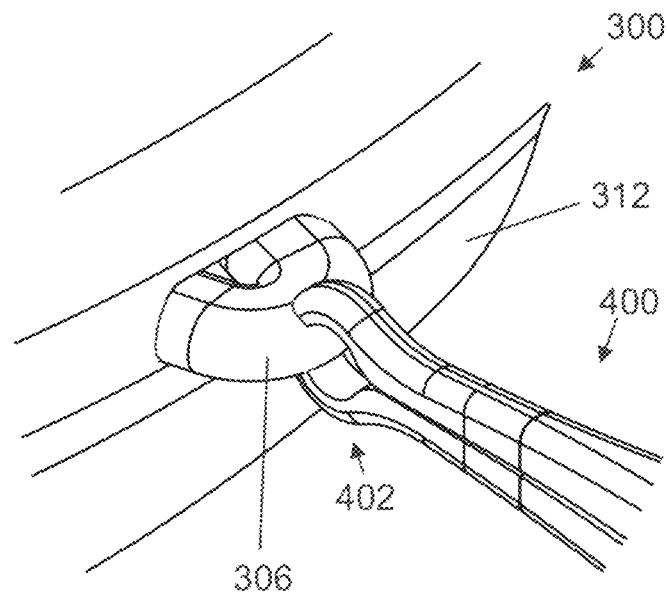
FIG. 49 is a perspective view of the distal portion of a metal vasectomy ring clamp with an insulated distal portion isolating a vas outside the scrotum in vasectomy procedures of the present invention.
Figure 50:
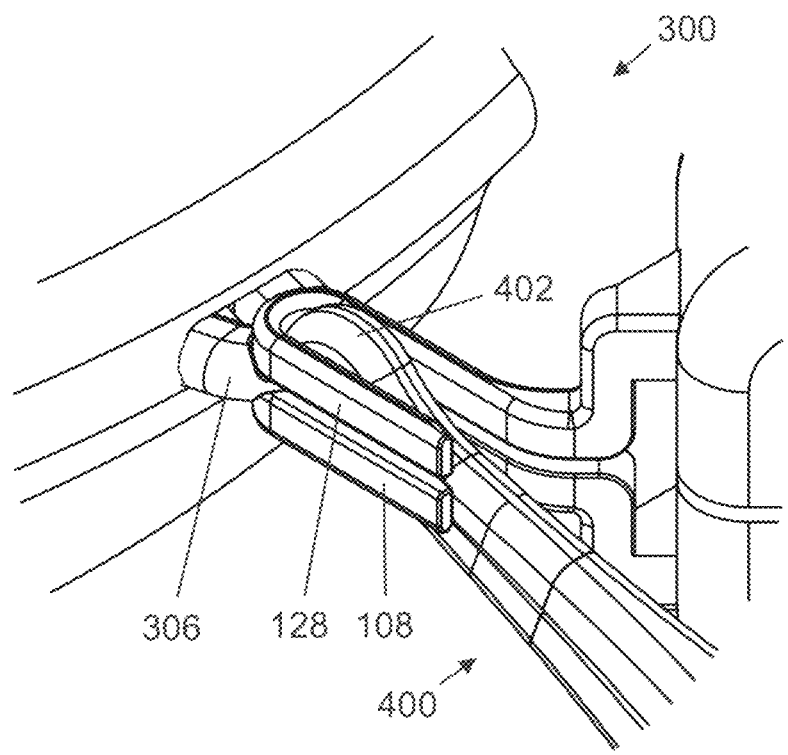
FIG. 50 is a perspective view of the vasectomy ring clamp and scrotum with the clamp and scrotum of FIG. 49 positioned in the jaws of a bipolar sealing device in preparation for sealing.
Figure 51:
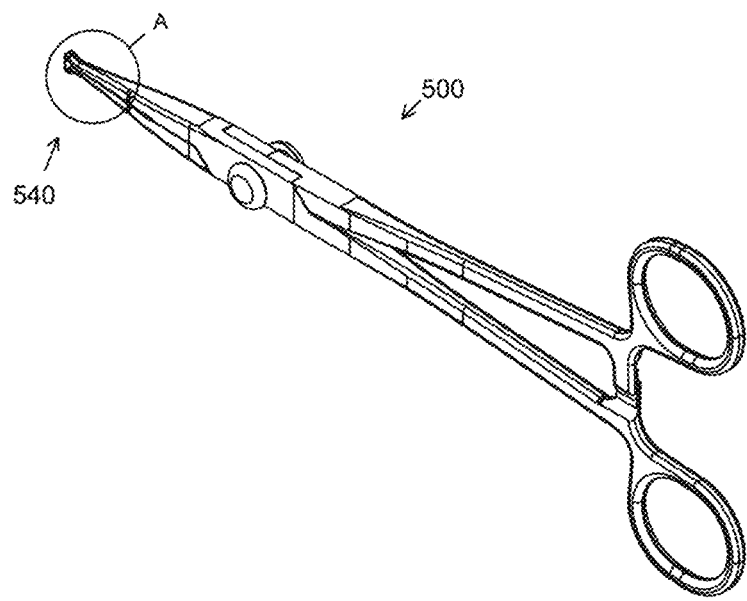
FIG. 51 is a perspective view of a metal tenaculum with an insulated distal portion for use in vasectomies using methods of the present invention.
Figure 52:
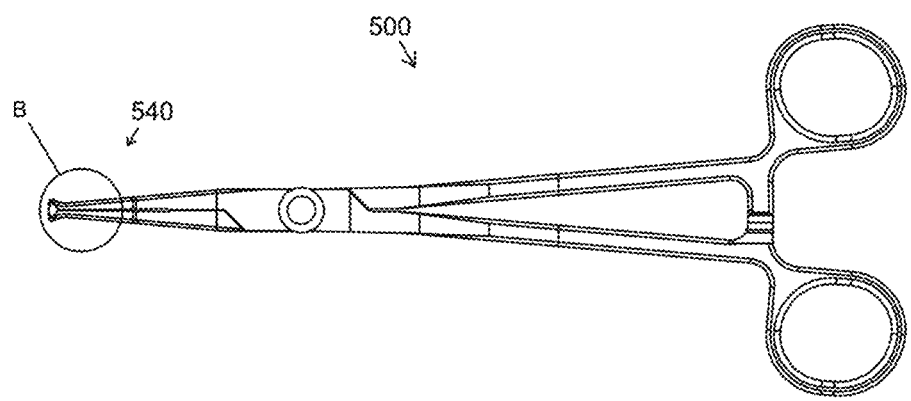
FIG. 52 is a side elevational view of the objects of FIG. 51.
Figure 53:
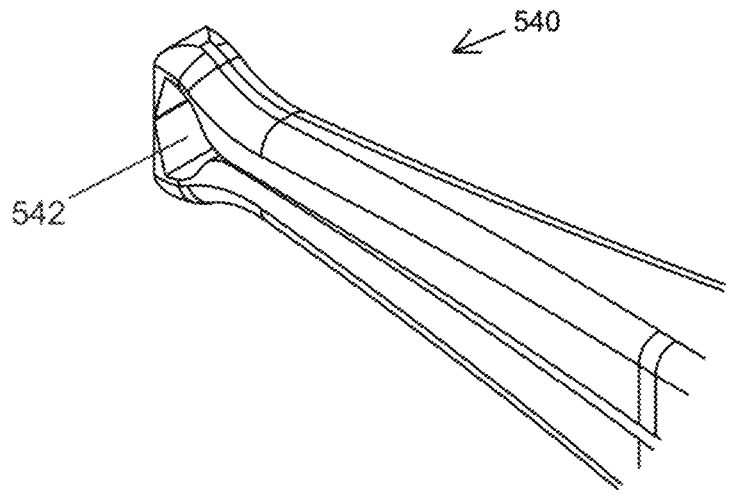
FIG. 53 is an expanded view of the objects of FIG. 51 at location A.
Figure 54:
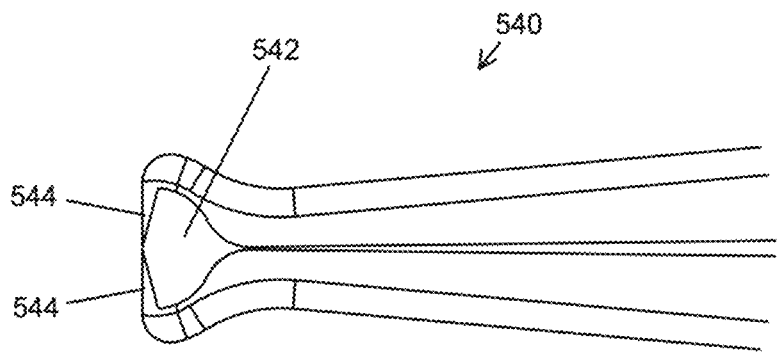
FIG. 54 is an expanded view of the objects of FIG. 52 at location B.

FIG. 49 depicts the distal portion of a ring forceps 400 isolating duct 306 outside outer wall 312 of scrotum portion 300. Distal-most portion 402 of rings forceps 400 is covered with an insulating coating. Critically, portion 402 should be configured to fit in slot 109 of jaw 108 (see FIG. 18). FIG. 50 depicts duct 306 positioned in jaws 108 and 128 of bipolar sealing device 100 in preparation for sealing. When a coated metal instrument like ring clamp 400 is used, it is not necessary to replace the metal instrument with a non-conductive clamp prior to sealing. Indeed, when ring clamp 400 is inserted into scrotum 300 as depicted in FIGS. 32 and 33, and brought external to the scrotum as in FIGS. 34 and 35, the clamping surfaces of distal portion 402 of clamp 400 may be directly positioned on the centerline of the duct as in FIG. 49, thereby saving procedure time.

Figure 55:
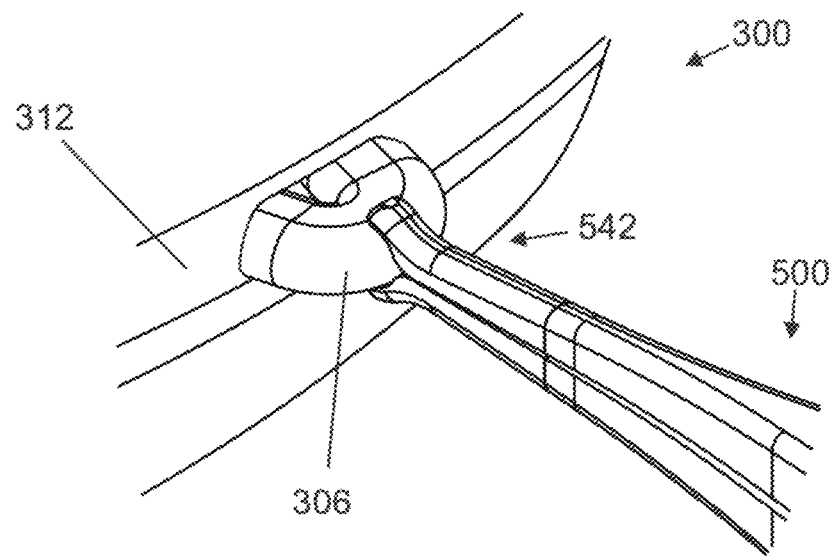
FIG. 55 is a perspective view of the distal portion of the tenaculum of FIG. 51 isolating a vas outside the scrotum in vasectomy procedures of the present invention.
Figure 56:
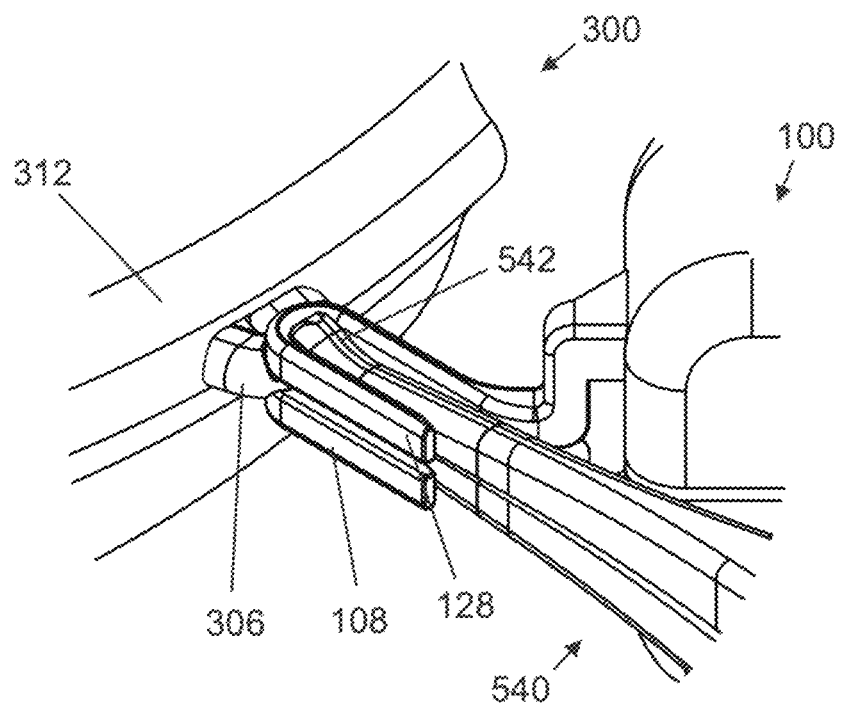
FIG. 56 is a perspective view of the vasectomy ring tenaculum and scrotum of FIG. 55 with the tenaculum and scrotum positioned in the jaws of a bipolar sealing device in preparation for sealing.
Figure 57:
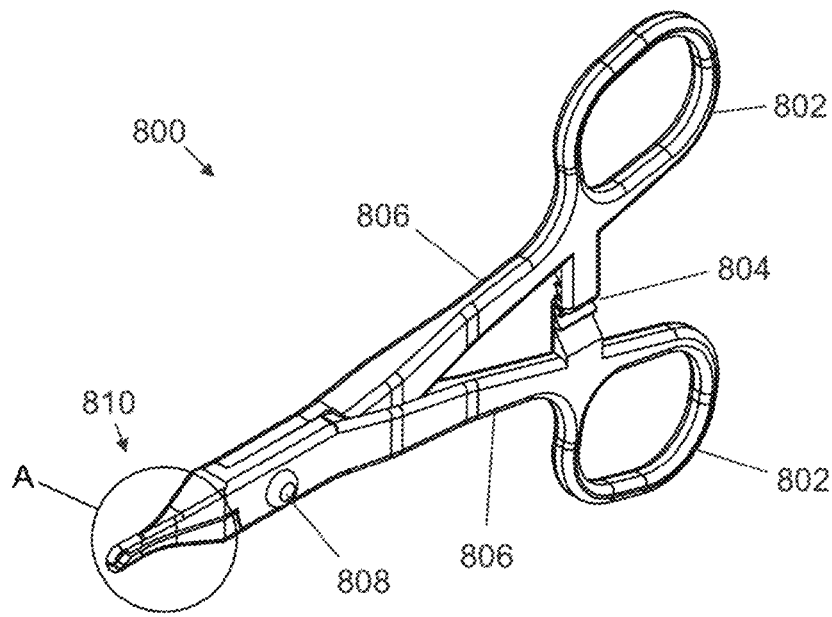
FIG. 57 is a perspective view of another clamp for use in methods of the present invention.
Figure 58:
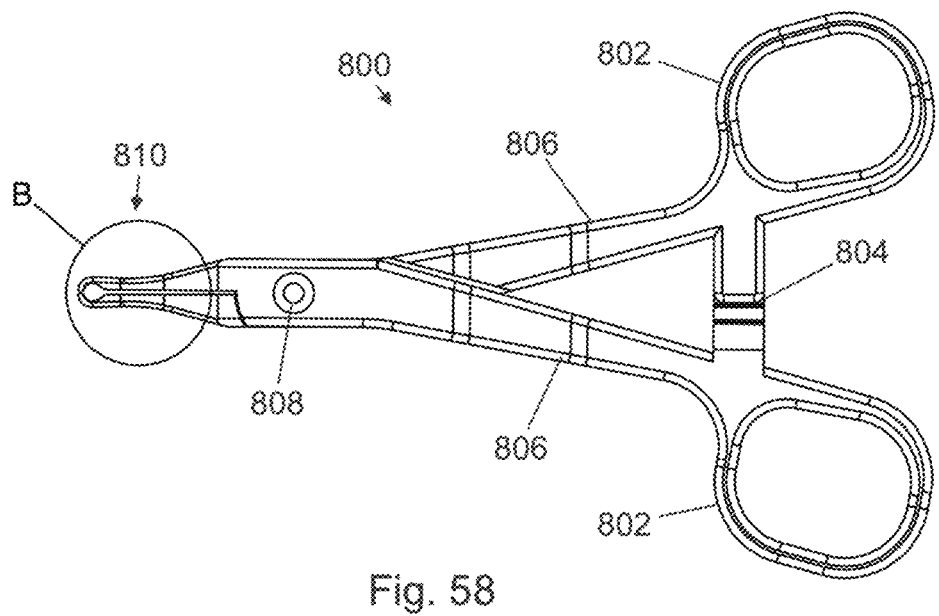
FIG. 58 is a side elevational view of the objects of FIG. 57.
Figure 59:
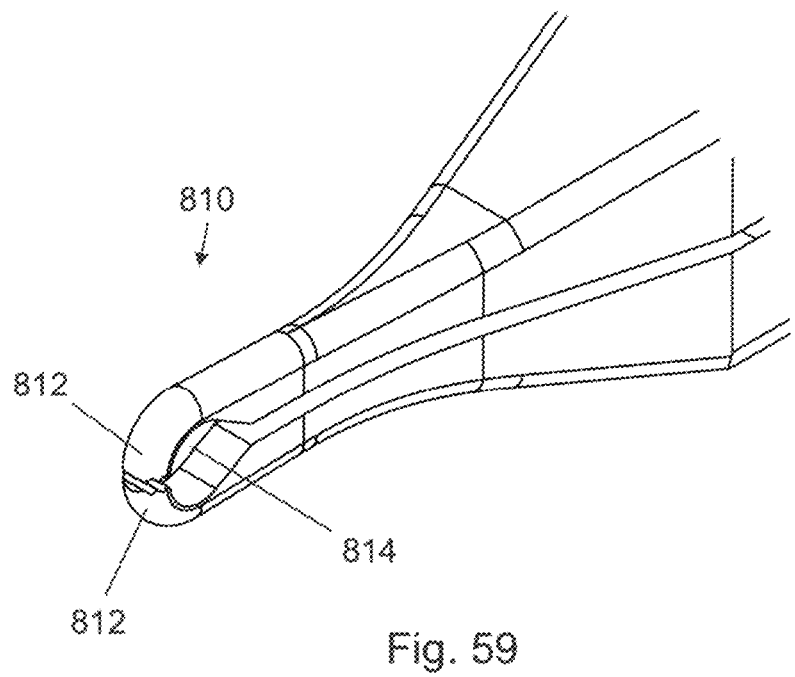
FIG. 59 is an expanded view of the objects of FIG. 57 at location A.
Figure 60:
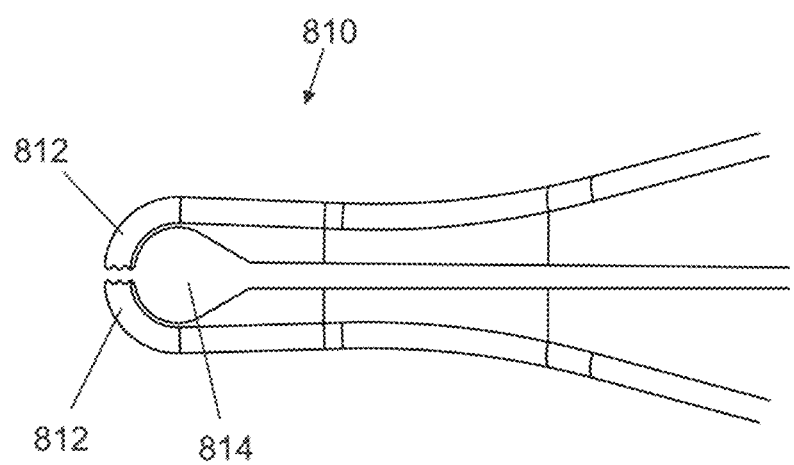
FIG. 60 is an expanded view of the objects of FIG. 58 at location B.

Another instrument useful in connection with the vasectomy methods of the present invention is depicted in FIGS. 51-54. Tenaculum 500 is like a ring forceps in all aspects except for the distal-most portion 540. Distal-most portion 540 has two opposed sharpened elements 544 that define a semicircular opening 542. Opening 542 is configured so that when tenaculum distal-most portion 540 of tenaculum 500 is inserted into opening 514 of outer scrotal wall 512 (see FIGS. 30 and 31) to grasp duct 308 in sheath 306, opening 542 limits the distance that duct 308 and sheath 306 can be positioned in distal-most portion 540. When tenaculum 500 is closed on the duct, opposed sharpened elements 544 penetrate duct 308 and its surrounding sheath 306 at or near the midpoint of duct 308. Duct 308 and sheath 306 are then withdrawn as depicted in FIG. 55 and positioned in jaws 108 and 128 as shown in FIG. 56 in preparation for sealing. Because the opening 514 is depth limiting and sharpened elements 544 penetrate the duct at its centerline, it is not necessary to visualize the duct when delivering it via opening 314 in scrotum outer wall 312. Disruption of nerves 58 in sheath 52 (see FIG. 12) is minimized since distal-most portion 540 of tenaculum 500 ends at cutting elements 544 that are positioned at the midline of duct 54 (FIG. 12).

Figure 66:
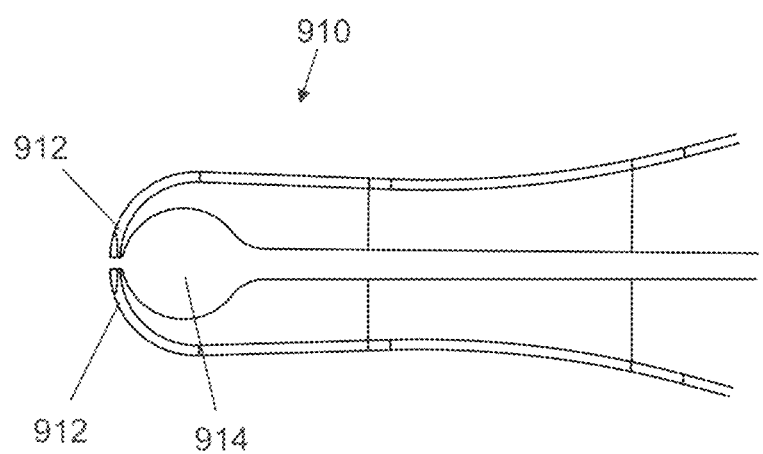
FIG. 66 is an expanded view of the objects of FIG. 64 at location B.
Figure 67:
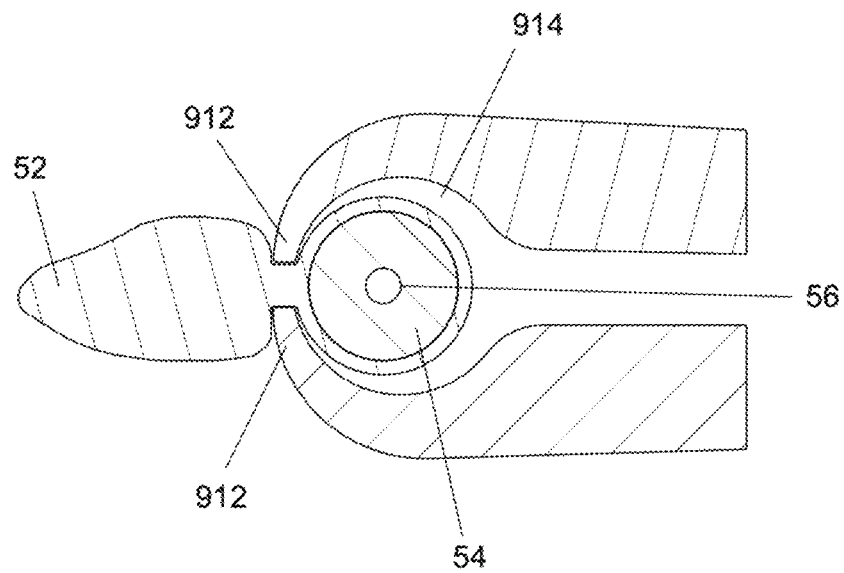
FIG. 67 is a sectional depiction of a vas duct and sheath positioned within the distal clamping surfaces of the clamp of FIG. 63 in preparation for placing the bipolar jaws of a coagulating device in a vasectomy method of the present invention.
Figure 68:
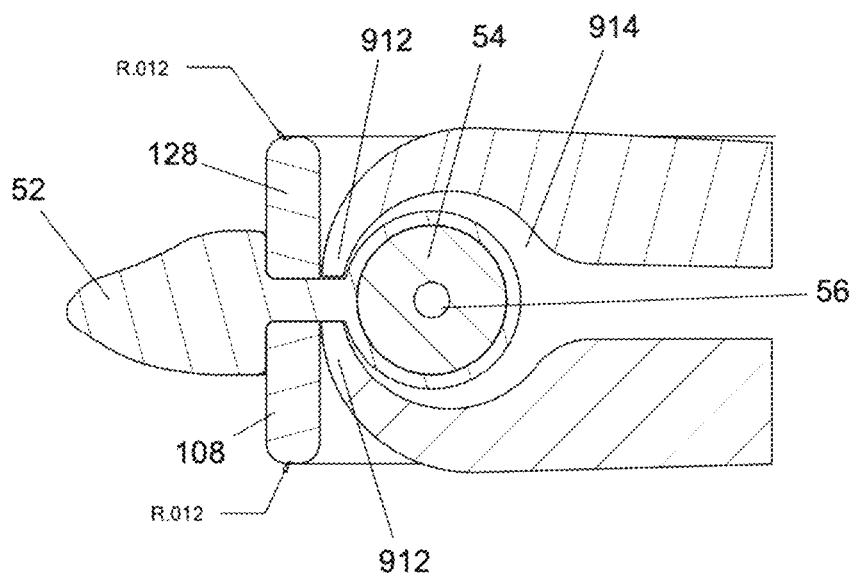
FIG. 68 depicts the objects of FIG. 67 wherein the bipolar jaws of a coagulating device are positioned in preparation for sealing of the duct in a vasectomy method of the present invention.

FIGS. 63 through 66 depict a clamp 900 for use in vasectomies using methods of the present invention wherein the distal clamping surfaces are not positioned on the vas duct within the sheath, but rather distal to the duct. Clamp 900 is identical in all aspects of form and function to clamp 800 (see FIGS. 57 to 60) except as specifically hereafter described. As best seen in FIG. 66, the distal clamping portions 912 of distal portion 910 has a reduced cross-section when viewed as in FIG. 64, and opening 914 is configured to accept a complete vas duct and the surrounding adjacent portion of a vas sheath therein. FIG. 67 is a sectional depiction of a vas duct 54 with lumen 56 within vas sheath 52 clamped between clamping portions 912 of clamp 900, clamping portions 912 being positioned distal to duct 54 in a vasectomy method of the present invention. Duct 54 and the proximal portion of sheath 52 surrounding it are positioned in opening 914 of clamp 900. In FIG. 68, jaws 108 and 128 of bipolar sealing device 100 (FIGS. 15 to 20) are positioned around clamping portions 912 of 900 positioned in FIG. 67 in preparation for sealing of duct 54 and the portions of sheath 52 compressed between jaws 108 and 128. Nerves within the portion of sheath 52 distal to jaws 108 and 128 will be unaffected or undergo RF neurotomy as in previously described embodiments.

Figure 61:
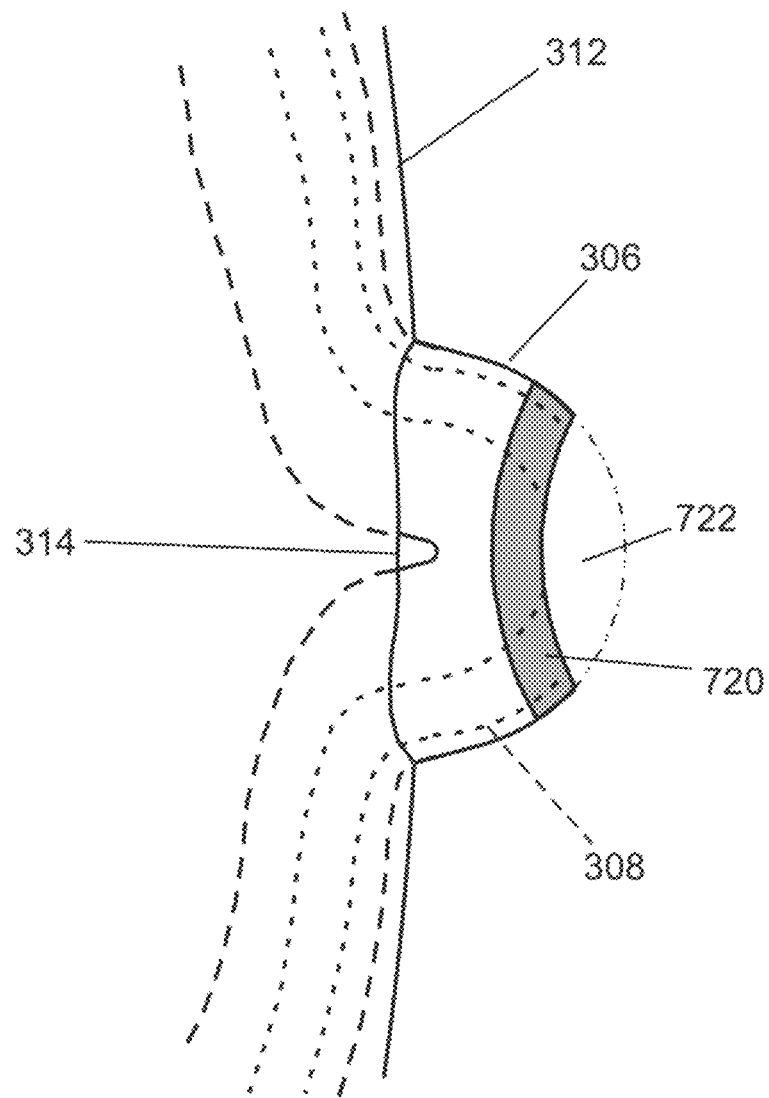
FIG. 61 is a plan view depiction of the site of a completed vasectomy of the present invention performed using a bipolar sealing device in which the jaws have an alternate configuration.
Figure 62:
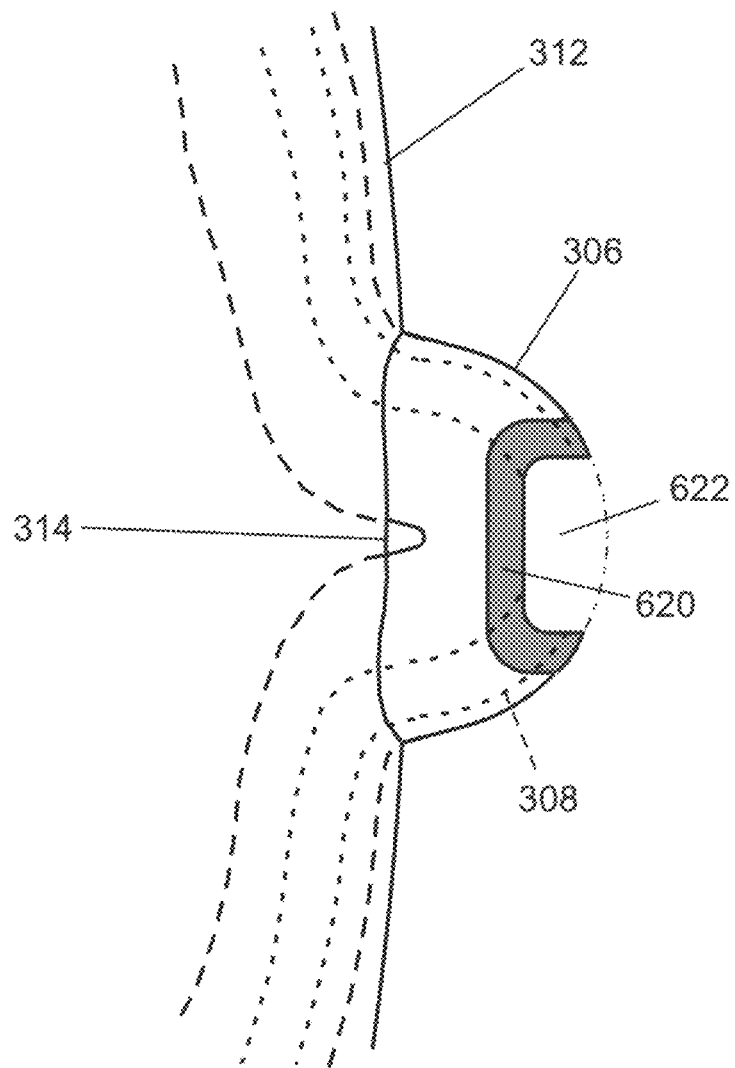
FIG. 62 is a plan view depiction of the site of a completed vasectomy of the present invention performed using a bipolar sealing device in which the jaws have a second alternate configuration.
Figure 63:
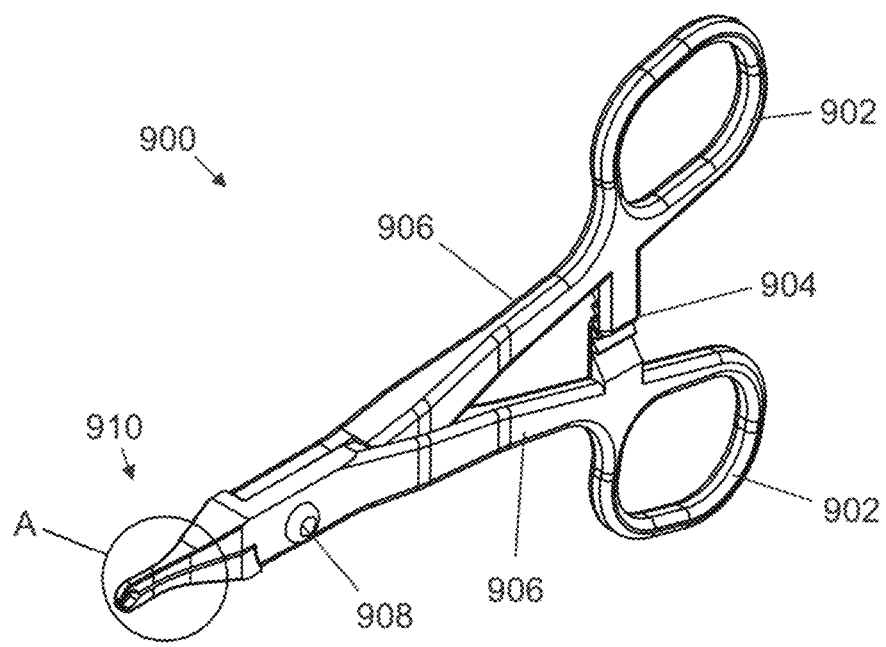
FIG. 63 is a perspective view of another clamp for use in vasectomy methods of the present invention.
Figure 64:
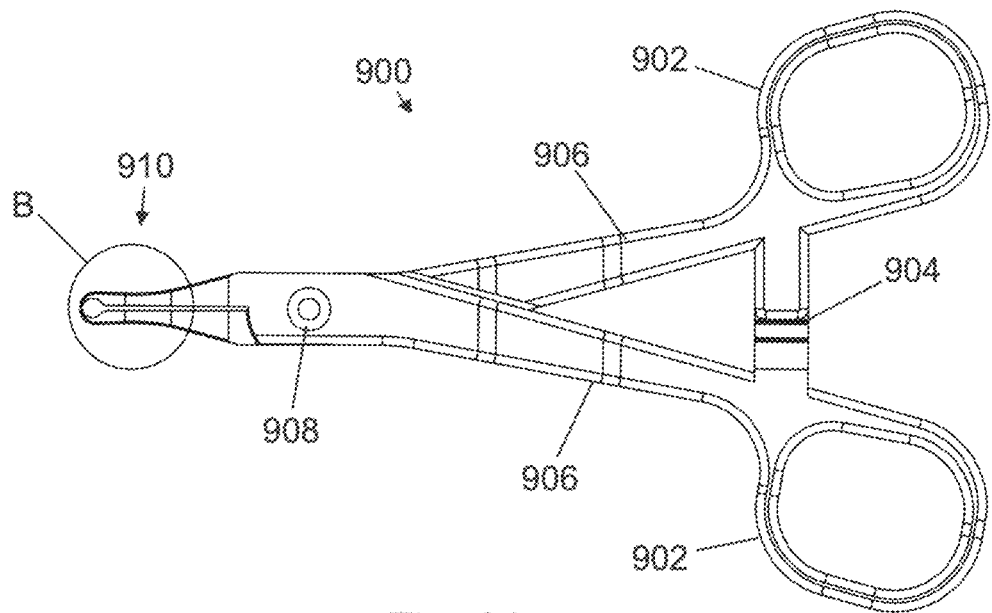
FIG. 64 is a side elevational view of the objects of FIG. 63.
Figure 65:
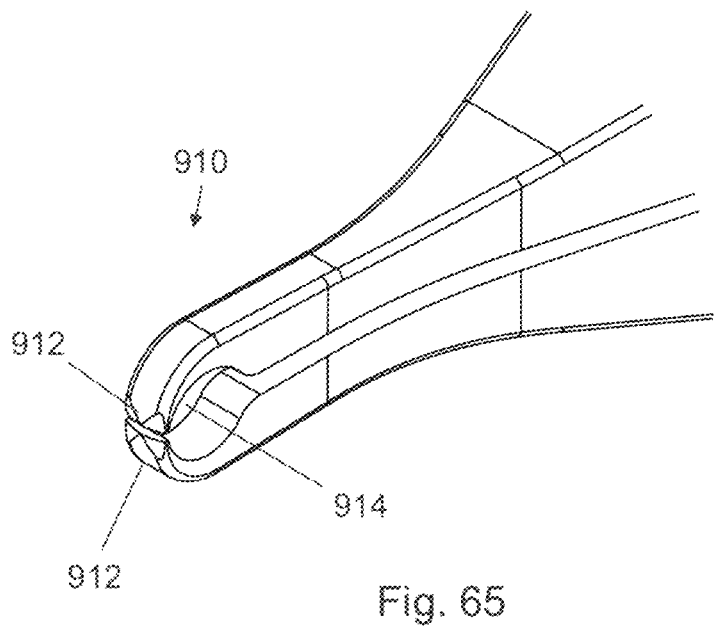
FIG. 65 is an expanded view of the objects of FIG. 63 at location A.

In methods of the present invention previously described, referring to FIG. 48, sealed region 320 containing portions of duct 308 and sheath 306 has an arcuate form. In other embodiments the sealed region may have other forms selected to achieve specific objectives. For instance, some clinicians may wish to excise a greater length of duct 308 to possibly reduce the chances of recanalization, a vasectomy failure in which the ends of duct 308 spontaneously reconnect and reestablish the flow of sperm. The jaws of the bipolar sealing device may be configured to achieve this and other objectives. For instance, FIG. 61 depicts a sealed portion 720 with an arcuate shape with a large radius such that excised portion 722 contains a larger length of duct 308 than in FIG. 48. Indeed, the radius of excised portion may be increased so as to be a straight line. In FIG. 62 region 620 has a form comprising linear portions joined by radii. As with excised portion 722 of FIG. 61, excised portion 622 contains an extended length of duct 308.

In methods of the present invention, a clamp is positioned on a vas duct or distal to the duct, through the sheath containing it, and without delivering the duct from the sheath. Thereafter the jaws of an RF bipolar sealing device are positioned so that at least a portion of the jaws is distal to the previously placed clamp and a portion of the vas duct is clamped between the bipolar jaws. Subsequently RF energy seals the tissue between the bipolar jaws to create a sealed region thereby occluding the vas duct. Any vasectomy method comprising these steps falls within the scope of this invention regardless of the shape of the sealed region.

INDUSTRIAL APPLICABILITY

As noted previously herein, by eliminating the steps of scrotal dissection and vas duct extraction, the vasectomy methods of the present invention overcome disadvantages and deficiencies of conventional vasectomy methods, providing a rapid, reliable, minimally-invasive male sterilization procedure that significantly reduces or eliminates negative side effects, including swelling and spontaneous regeneration, and minimizes recovery time and recovery restrictions. In addition, the method of the present invention take efforts to minimize contact with the distal wall of the vas sheath so to avoid and/or minimize injury or trauma to adjacent nerve endings and thereby minimize post-surgical pain. Finally, the methods of the present invention further avoid exposure to patient bodily fluids, thereby minimizing the potential for transmission of blood-borne diseases such as HIV and Hepatitis.

Due to the complications associated with traditional vasectomies but eliminated by the techniques and devices herein disclosed, successful procedures have, in the past, required the utilization of skilled experienced surgeons. However, the vasectomy method of the instant invention minimizes the number of steps and duration of the procedure, thereby allowing the procedure to be quickly completed by clinicians with minimal training. Moreover, given its simplicity, less skilled heath care workers can master the procedure in a relatively short period of time. This will extend the feasibility of male sterilization to areas of the world where doctors, more particularly skilled surgeons, are in short supply. For example, the method of the instant invention may be advantageously used for family planning in developing countries.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. A method for performing a vasectomy comprising the steps of:
   a. locating a length of a vas deferens within a scrotum, wherein said vas deferens is characterized by an outer vas sheath disposed about an inner vas duct, further wherein said inner vas duct is characterized by curved proximal and distal walls that meet at a midline to form an integral tubular channel;
   b. dissecting said length of vas deferens from the scrotum;
   c. placing a tissue-capturing distal portion of a surgical clamp approximately about said midline of said inner vas duct contained within said length of vas deferens dissected from the scrotum in step (b) so as to temporarily isolate a portion of vas tissue that includes both proximal and distal walls of said inner vas duct but excludes at least part of a distal region of said outer vas sheath;
   d. providing a coagulating bipolar device having a proximal handle portion that defines a longitudinal axis of said device and an active distal portion characterized by a pair of opposingly-faced, upper and lower coagulating jaws, wherein each of said jaws is movable between open and closed positions, and (ii) provided with mating inner edges, whereby, when said jaws are in the closed position and viewed in a plan view, said inner-facing cutting edges engage to define an interior perimeter comprised of (1) a central slot that is angularly offset from said longitudinal axis and (2) a lateral opening that permits said distal clamping portion to be positioned around said tissue-capturing distal portion of said surgical clamp that retains said isolated portion of vas tissue;
   e. tightly closing said jaws about the tissue-capturing distal portion of said surgical clamp to thereby define a first area of clamped vas tissue disposed between said closed jaws and a second area defined by said interior perimeter that includes said isolated portion of vas tissue retained by said tissue-capturing distal portion of said surgical clamp; and f. activating said coagulating bipolar device so as to coagulate said first area of clamped vas tissue.

2. The vasectomy method according to claim 1, wherein said method further comprises the steps of:
   (g) excising some or all of the second area of said isolated portion of vas tissue that includes both proximal and distal walls of said inner vas duct but excludes at least part of said distal region of said outer vas sheath; and
   (h) removing said upper and lower jaws from the clamped vas tissue immediately after step (f).

3. The vasectomy method according to claim 1, wherein said inner vas duct is retained within said outer vas sheath for the duration of the procedure.

4. The method according to claim 1, wherein said locating step (a) further includes the step of manipulating said inner vas duct into a fold of scrotal tissue in a high lateral position.

5. The method according to claim 1, wherein said surgical clamp is placed medially adjacent to the vas duct.

6. The method according to claim 1, wherein said surgical clamp is a ring forceps.

7. The method according to claim 6, wherein a distal end of said ring forceps is placed at said midline of said inner vas duct so as to compress said vas duct between opposed clamping faces of said ring forceps.

8. The method according to claim 1, wherein said surgical clamp is a tenaculum.

9. The method according to claim 8, wherein sharpened portions of said tenaculum penetrate the vas duct in said midline of said inner vas duct.

10. The method according to claim 1, wherein said inner edges of said pair of opposingly-faced, upper and lower coagulating jaws are sharpened so as to enable direct excision of said second area that includes said isolated portion of vas tissue that includes both proximal and distal walls of said inner vas duct but excludes at least part of said distal region of said outer vas sheath.

11. The vasectomy method according to claim 1, wherein said coagulation of said first area of clamped vas tissue serves to both bisect the vas duct into separated abdominal and testicular legs and deaden sensory nerves located in the distal region of said outer vas sheath.

12. The vasectomy method according to claim 1, wherein said upper and lower jaws as well as said first area of clamped tissue are arcuate in shape such that said second area comprises a convex region.

* * * * *